United States Patent [19]
Ledbetter et al.

[11] Patent Number: 6,010,902
[45] Date of Patent: Jan. 4, 2000

[54] ANTIBODY HETEROCONJUGATES AND BISPECIFIC ANTIBODIES FOR USE IN REGULATION OF LYMPHOCYTE ACTIVITY

[75] Inventors: Jeffrey A. Ledbetter; Lisa K. Gilliland, both of Seattle, Wash.

[73] Assignee: Bristol-Meyers Squibb Company, Princeton, N.J.

[21] Appl. No.: 08/366,401

[22] Filed: Dec. 29, 1994

Related U.S. Application Data

[63] Continuation of application No. 08/028,527, Mar. 9, 1993, abandoned, which is a continuation of application No. 07/880,307, May 5, 1992, abandoned, which is a continuation of application No. 07/733,369, Jul. 19, 1991, abandoned, which is a continuation of application No. 07/424,801, Oct. 20, 1989, abandoned, which is a continuation-in-part of application No. 07/271,934, Nov. 14, 1988, abandoned, which is a continuation-in-part of application No. 07/176,825, Apr. 4, 1988, abandoned.

[51] Int. Cl.$^7$ ............................... C12N 5/00; C12N 5/02; C07K 16/00; C12P 21/08
[52] U.S. Cl. ........................... 435/328; 435/332; 435/334; 530/388.75; 530/391.1; 530/405; 530/387.3
[58] Field of Search ............................. 424/144.1, 179.1; 435/240.27, 328, 332, 334; 530/388.75, 391.1, 405, 387.3

[56] References Cited

U.S. PATENT DOCUMENTS

| | | |
|---|---|---|
| 4,381,292 | 4/1983 | Bieber et al. . |
| 4,676,980 | 6/1987 | Segal ................................. 424/85.91 |

FOREIGN PATENT DOCUMENTS

| | | | |
|---|---|---|---|
| 0153871 | 2/1985 | European Pat. Off. | ........ A61K 39/00 |
| 0235805 | 3/1987 | European Pat. Off. | ...... A61K 39/395 |
| 0241907 | 4/1987 | European Pat. Off. | ...... A61K 39/395 |
| 8504811 | 11/1985 | WIPO | ........................... A61K 39/395 |

OTHER PUBLICATIONS

V. Ghetie & I. Moraru, "Preparation and Applications of Multivalent Antibodies with Dual Specificity," Meth. Enzymol. 92:523–543 (1983).
Kimball, Ed., Intro to Immunol. 2nd Ed., Chpt. 11–13, MacMillan Pub. Co. (1986).
Reinherz et al., "Clonotypic Surface Structure on Human T Lymphocytes: Functional and Biochemical Analysis of the Antigen Receptor Complex", Immunol. Rev:81:95–129 (1984).
Emmrich et al., "Cross–Linking of the T–Cell Receptor Complex with the Subset–Specific Differentiation Antigen Stimulates Interleukin 2 Receptor Expression in Human CD4 and CD8 T Cells", Eur. J. Immunol. 17:529–34 (1987).
Anderson et al., "Cross–Linking of T3 (CD3) with T4 (CD4) Enhances the Proliferation of Resting T Lymphocytes" J. Immunol.,139(No.3) 678–83 (1987).
McMichael, Ed., (Cobbold) Leukocyte Typing III, Oxford Univ. Press, Oxford, U.K., (1987), Chpt. 15, pp. 788–803.

Ledbetter et al., Perspectives in Immunogen. and Histocompatibility, vol. 6, Heise, Ed., "Lymphocyte Surface Antigens" (1984), pp. 325–340 (N.Y. 1984).
Yamada et al., "Monoclonal Antibody 9.3 and Anti–CD11 Antibodies Define Reciprocal Subsets of Lymphocytes", Eur. J. Immunol, 15:1164–1169 (1985).
Imboden et al., "Transmembrane Signalling by the T Cell Antigen Receptor" J. Exp. Med., 161:446–56 (1985).
Imboden et al., "Antigen Recognition by a Human T Cell Clone Leads to Increases in Inositol Triphasphate" J. Immunol. 103(No.5): 1322–24 (1987).
Walker et al., "Activation of T Cells by Cross–Linking an Anti–CD3 Antibody with a Second Anti–T Cell Antibody: Mechanism and Subset–Specific Activation", Eur. J. Immunol. 17:873–80 (1987).
Ledbetter et al., "Valency of CD3 Binding and Internaliztion of the CD3 Cell–Surface Complex Control T Cell Responses to Second Signals", J. Immunol., 136:3945–52 (1986).
Marrack et al., "The Major Histocompatibility Complex Restricted Antigen REceptor on T Cells II. Role of the L3T4 Product", J. Exp. Med., 158:1077–91 (1983).
Gay et al., "Functional Interaction Between Human T Cell Protein CD4 and the Major Histocompatibility Complex HLA–DR Antigen" Nature, 328:626–29 (1987).
Regnier–Vigruroux et al., "Accessory Molecules and T Cell Activation I. Antige Receptor Avidity Differentially Influences T Cell Sensitivity to Inhibition by Monoclonal Antibodies to LFA–1 and L3T4", Eur. J. Immunol., 16:1385–90 (1986).
Shaw et al., "Susceptibility of Cytotoxic T Lymphocyte (CTL) Clones to Inhibition by Anti–T3 and Anti–T4 (But not Anti–LF–1) Monoclonal Antibodies Varies with the Avidity of CTL–Target Interaction", J. Immunol. 134(No.5): 3019–26 (1985).
Bank et al., "Perturbation of the T4 Molecule Transmits A Negative Signal to the T Cells" J. Exp. Med., 162:1294 (1985).

(List continued on next page.)

Primary Examiner—Toni R. Scheiner
Assistant Examiner—Sheela J. Huff
Attorney, Agent, or Firm—Merchant, Gould, Smith, Edell, Welter & Schmidt

[57] ABSTRACT

The present invention relates to novel antibody heteroconjugates and bispecific antibodies and methods and compositions and their use in the enhancement or inhibition of activation and function of T or B lymphocytes. The heteroconjugates are comprised of at least two antibody molecules cross-linked to each other, each molecule being reactive with a different lymphocyte antigen on the same cell. The invention also provides bispecific antibodies comprising a first binding region reactive with an antigen on a lymphocyte and a second binding region reactive with a different antigen on the lymphocyte. The heteroconjugates, bispecific antibodies, methods and compositions of this invention are therefore useful in the regulation of lymphocyte function, resulting in the improvement of cellular immune responses in various disease states.

28 Claims, 12 Drawing Sheets

OTHER PUBLICATIONS

Tite et al., "The Role of L3T4 in T Cell Activation: L3T4 May be Both An Ia–Binding Protein and a Receptor That Transduces a Negative Signal" *J. Cell Mol. Immunol.*, 2:179–90 (1986).

Rosoff et al., "The Role of the L3T4 Molecule in Mitogen and Antigen Activated Signal Transduction" Cell. 49:845–53 (1987).

Trowbridge et al., "Differences in the Surface Proteins of Mouse B and T Cells" *Proc. Natl. Acad. Sci. USA* 72:157–161 ( 1975).

Komuro et al., "Ly–5: A new T–Lymphocyte Antigen System", *Immunogenetics* 1:452–456 (1975).

Schied et al., "Further Description of the Ly–5 System", *Immunogenetics*, 9:423–433 (1979).

Dalchau et la., "Monoclonal Antibodies to a Human Leukocyte–Specific Membrane Glycoprotein Probably Homologous to the Leukocyte–Common (L–C) Antigen of the Rat", *Eur. J. Immunol*, 10:737–744 (1980).

Omary et al., "Human Homologue of Murine T200 Glycoprotein", *J. Exp. Med.*, 152:842–852 (1980).

Dalchau et al., "Identification with a Monoclonal Antibody of a Predominantly B Lymphocyte–Specific Determinant of the Human Leukocyte Common Antigen", *J. Exp. Med.* 153:753–765 (1981).

Morimoto et al., "The Isolation and Characterization of the Human Suppressor Inducer T Cell Subset", *J. Immunol.*, 134:1508–1515 (1985).

Ledbetter et al., "Antibodies to Common Leukocyte Antigen p220 Influence Human T Cell Proliferation by Modifying IL 2 Receptor Expression", *J. Immunol.*, 135: 1819–1825 (1985).

Smith et al., "Functional Subset of Human Helper–Inducer Cells Defined by a New Monoclonal Antibody UCHL1", *Immunol.*, 58:63–70 (1986).

Thomas et al., "Evidence from cDNA Clones that The Rat Leukocyte–Common Antigen (T200) Spans the Lipid Bilayer and Contains A Cytoplasmic Domain of Mr", *Cell*, 41:83–93 (1985).

Barclay et al., "Lymphocyte specific Heterogeneity in the Rat Leukocyte Common Antigen (T200) is Due to Differences in Polypeptide Sequences near the NH2–Terminus", *EMBO J.*, 6:1259–1264 (1987).

Saga et al., "Sequences of LY–5 cDNA: Isoform–Related Diversity of LY–5–mRNA" *Proc. Natl. Acad. Sci. USA*, 83:6940–6944 (1986).

Raschke, "Cloned Murine T200 (Lv-5) cDNA reveals Multiple Transcripts within B–and T–Lymphocyte Lineages", *Proc. Natl. Acad. Sci. USA*,84:161–165 (1987).

Thomas et al., "B–Cell Variant of Mouse T200 (Ly–5): Evidence for alternative mRNA spicing", *Proc. Natl. Acad. Sci. USA* 84:5360–5363 (1987).

Saga et al., "Alternative Use of 5' Exons in The Specification of Ly–5 Isoforms Distinguishing Hematopoietic Cell Lineages", *Proc. Natl. Acad. Sci. USA*, 84:5364–5368 (1987).

Ralph et al., "Structural Variants of Human T200 Glycoprotein (Leukocyte–Common Antigen)", *EMBO J.*,6:1251–1257 (1987).

Streuli et al., "Differential Usage of Three Exons Generates at Least Five Different mRNAs Encoding Human Leukocyte Common Antigens", *J. Exp. Med.*, 166:1548–1566 (1987).

Harp et al., "Inhibition of T Cell Responses to Alloantigens and Polyclonal Mitogens by Ly–5 Antisera" *J. Immunol.*, 133:10–15 (1984).

Bernabeu et al., "Interaction Between the CD45 Antigen and Phytohemagglutinin Inhibitory Effect on the Lectin–Induced T Cell Proliferation by anti–CD45 Monoclonal Antibody", *Eur. J. Immunol.*, 17:1461–1466 (1987).

Mittler et al., "Antibodies to the Common Leukocyte Antigen (T200) Inhibit an Early Phase in the Activation of Resting Human B Cells", *J. Immunol.*, 138:3159–3166 (1987).

Yakura, "On the Function of Ly–5 In the Regulation of Antigen–Driven B Cell Differentiation", *J. Exp. Med.*, 157:1077–1088 (1983).

Seaman et al., "Surface Antigens on Mouse Natural Killer Cells: Use of Monoclonal Antibodies to Inhibit or to Enrich Cytotoxic Activity" *J. Immunol.*, 127:982–986 (1981).

Newman, "Selective Blockade of Human Natural Killer Cells by a Monoclonal Antibody", Proc. Natl. Acad. Sci USA 79:3858–3862 (1982).

Makavama et al., "Cytotoxic T Cells Lyt Phenotype and Blocking of Killing Activity by Lyt Antisera", *Proc. Natl. Acad. Sci. USA*, 76:1977–1981 (1979).

LeFrancois et al., "Functional Modifications of Cytotoxic T–Lymphocyte T200 Glycoprotein Recognized by Monoclonal Antibodies", *Nature* (London) 314:449–452 (1985).

Martorell et al., "A Second Signal for T Cell Mitogenosis Provided by Monoclonal Antibodies", *Eur. J. Immunol.* 17:1447–1451 (1987).

Tonks et al., "Purification of the Major Protein–Tyrosine-–Phosphatases of Human Placenta", *J. Biol. Chem.*, 263:6722–6730 (1990).

Charbonneau et al., "The Leukocyte Common Antigen (CD45): A Putative Receptor–Linked Protein Tyrosine Phosphatase",*Proc. Natl. Acad. Sci. USA*, 85:7182–7186 (1988).

Kunfer et al., "Coclustering of CD4 (L3T4) Molecule with the T–Cell Receptor is Induced by Specific Direct Interaction of Helper T Cells and Antigen–Presenting Cells" *Proc. Natl. Acad. Sci. USA*, 84:5888–5892 (1987).

Klausner et al., "T Cell Receptor Tyrosine Phosphorylation", *J. Biol. Chem.* 262:12654–12659 (1987).

Rudd et al., "The CD4 Receptor is Complexed in Detergent Lysates to a Protein–Tyrosine Kinase (pp58) from Human T Lymphocytes", Proc. Natl. Acad. Sci USA 85:5190–5194 (1988).

Clark et al., "Hybrid Antibodies for Therapy", in Monoclonal Antibody Therapy Prog. Allergy, 45:31–49 (1988).

Clark et al., "T–Cell Killing of Target Cells Induced by Hybrid Antibodies: Comparison of Two Bispecific Monoclonal Antibodies", *JNCI*, 79:1393–1401 (1987).

Ledbetter et al., "Enhanced Transmembrane Signalling Activity of Monoclonal Antibody Heteroconjugates Suggest Molecular Interactions Between Receptors on the T Cell Surface" *Molecular Immunol.* 26(2):137–145 (1989).

Eichmann et al., "Distinct Functions of CD8 (CD4) are Utilized at Different Stages of T–Lymphocyte Differentiation" *Immunol. Rev.* 109:39–75 (1990).

Boyce and Eichmann, "Cross–Linking of Lyt–2 (CD8) to the T Cell Antigen Receptor Optimally Activates T Lymphocytes" Trans. Proceedings 21:133–137 (1989).

Jonsson et al., "Immunoregulation Through CD8 (Ly–2): State of Aggregation with The β/CD3 T Cell Receptor Controls Interleukin 2–Dependent T Cell Growth" *Eur. J. Immunol.*, 19:253–260 (1989).

Wagner et al., "T Cell Receptors and Cellular Interactions", *Immunol. Today* 10:S25–S27 (1989).

Wong et al., "Characterization of the CD4+ and CD8+ Tumor Infiltrating Lymphocytes Propagated with Bispecific Monoclonal Antibodies" J. Immunol., 143:3404–3411 (1989).

Gilliland et al., "Composite Signal Transduction in T–Cell Activation: Enhancement, Inhibition, and Desensitization" in Ligands, Receptors and Signal Transduction in Regulation of Lymphocyte Function Cambier ed., pp. 321–357 (1990).

Rabinovitch et al., "Heterogeneity Among T Cells in Intracellular Free Calcium Responses After Mitogen Stimulation with PHA or ANti–CD3, Simultaneous Use of Inot–1 and Immunofluorescence with Flow Cytometry", J. Immunol., 137:952–61 (1986).

Ledbetter et al., "Crosslinking of Surface Antigens Causes Mobilization of Intracellular Ionized Calcium in T Lymphocytes", Proc. Natl. Acad. Sci USA, 84:1384–1388 (1987).

Samelson et al., "T Cell Antigen Receptor Phosphorylation Induced by an Anti–Receptor Antibody", J. Immunol., 139:2708–2714 (1987).

Hsi et al., "T Cell Activation Induces Rapid Tyrosine Phosphorylation of a Limited Number of Cellular Substrates", J. Biol. Chem., 264:10836–10842 (1989).

Barber et al., "The CD4 and CD8 Antigens Are Coupled to a Protein–Tyrosine Kinase ($p56^{lck}$) That Phosphorylates the CD3 Complex", Proc. Natl. Acad. Sci. USA, 86:3277–3281 (1989).

Segal et al., "Targeting of Cytotoxic Cells with Cross–linked Anbitody Heteroaggregates", Mol. Immunol., 23(11):1211–114 (1986), Abstract in Chemical Abstracts, 106(5):2 (1987).

Liu et al., "Heteroantibody duplexes target cells for lysis by cytotoxic T Lymphocytes" in Proc. Natl. Acad. Sci. USA 82(24):8648–52 (1985), abstract in Chemical Abstracts, 104:(12) 2 (1986).

Wong and Colvin, "Bi–Specific Monoclonal Antibodies: Selective Binding and Complement Fixation to Cells that Express Two Different Surface Antigens", J. Immunol., 139:1369–1374 (1989).

Ledbetter et al., "CD45 Regulates Signal Transduction and Lymphocyte Activation by Specific Association with Receptor Molecules on T or B Cells", Proc. Nat. Acad. Sci USA, 85:8628–8632 (1988).

Emmrich et al., "Selective Stimulation fo Human T Lymphocytes Subsets by Heteroconjugates of Antibodies to the T Cell Receptor and to Subset–Specific Differentiation Antigens", Eur. J. Immunol., 18:654–648 (1988).

Ledbetter et al., "Signal Transduction Through CD4 Receptors: Stimulatory vs. Inhibitory Activity is Regulated by CD4 Proximity to the CD3/T Cell Receptor", Eur. J. Immunol., 18:525–532 (1988).

Boyce et al., "Heterologous Cross–Linking of Lyt–2 (CD8) to the β–T Cell Receptor is More Effective in T Cell Activation Than Homologous β–T Cell Receptor Cross–Linking", J. Immunol., 141:2882–2888 (1988).

Waldman Science vol. 252 1657, 1991.

Hird et al. Genes and Cancer 1990 Wiley and Sons Ltd. 183.

Staerz and Bevan 1986 PNAS 1453.

Milstein and Cuello Nature 305 1987 p. 537.

Leucocyte Typing Human Leucocyte Differentiation Antigens Detected by Monoclonal Abies, Springer Verlag Berlin (1984), Bernard et al. (eds.).

Wong, J. Immunology, (1987) 139(4):1369–74.

Ledbetter, PNAS, (Mar. 1987) 84:1384–88.

Morrison Science vol. 229, p. 1202 1985.

Turka et al. The Journal of Immunology vol. 146, No. 5. 1428, 1991.

Methods in Enzymology. p. 523, Copyright 1983 Academic Press Inc. vol. 92 (Cited by applicant).

FIG. 11.
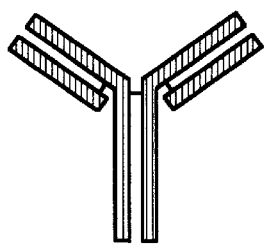
$L_1H_1H_1L_1$
Parental Mab 1
(Bivalent)
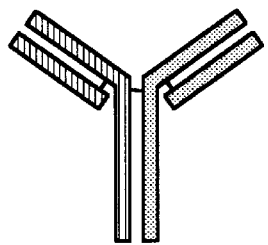
$L_1H_1H_2L_2$
Bispecific
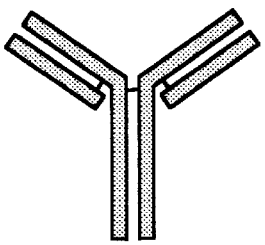
$L_2H_2H_2L_2$
Parental Mab 2
(Bivalent)
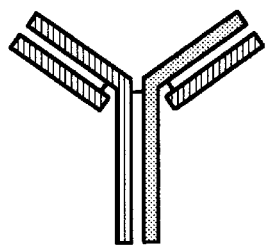 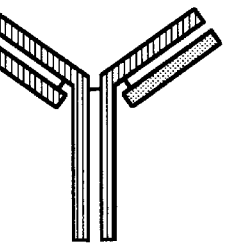 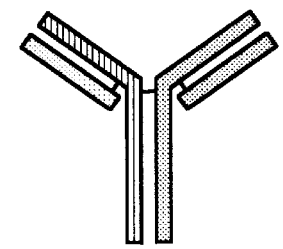 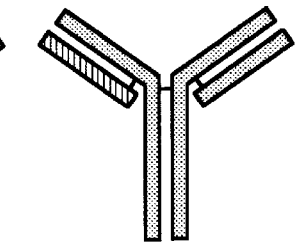
$L_1H_1H_2L_1$   $L_1H_1H_1L_2$   $L_2H_1H_2L_2$   $L_1H_2H_2L_2$
Monovalent
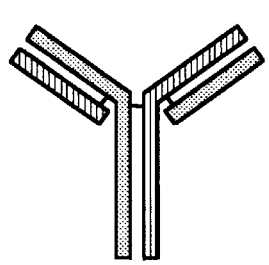 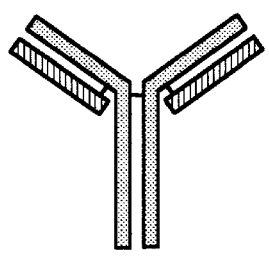 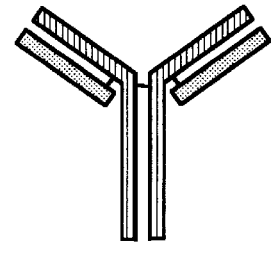
$L_1H_2H_1L_2$   $L_1H_2H_2L_1$   $L_2H_1H_1L_2$
Inactive

ANTIBODY HETEROCONJUGATES AND BISPECIFIC ANTIBODIES FOR USE IN REGULATION OF LYMPHOCYTE ACTIVITY

This is a continuation of application Ser. No. 08/028,527, filed Mar. 9, 1993, now abandoned, which is a continuation of application Ser. No. 07/880,307 filed on May 5, 1992, now abandoned, which is a continuation of application Ser. No. 07/733,369 filed on Jul. 19, 1991, now abandoned, which is a continuation of application Ser. No. 07/424,801 filed on Oct. 20, 1989, now abandoned, which is a continuation-in-part of U.S. patent application Ser. No. 271,934, filed Nov. 14, 1988, now abandoned, which is a continuation-in-part of U.S. patent application Ser. No. 176,825, filed Apr. 4, 1988, now abandoned, the disclosures of which are incorporated by reference herein.

TECHNICAL FIELD OF THE INVENTION

The present invention relates to novel antibody heteroconjugates and bispecific antibodies and their use in the regulation of the activity of lymphocytes such as T cells and B cells. More particularly, the invention relates to heteroconjugates comprised of at least two antibodies coupled to each other, each antibody being reactive with a different lymphocyte surface antigen. These heteroconjugates appear to act by binding to lymphocytes and bringing the respective cell surface antigens they react with into physical proximity to each other, resulting in enhanced or reduced signal transduction and proliferation of lymphocytes. According to a preferred embodiment of the invention, an antibody reactive with the T cell receptor or its associated CD3 complex is cross-linked to an antibody reactive with a second T cell surface antigen, such as CD2, CD4, CD6 or CD8 to enhance activation and function of T cells. According to another preferred embodiment, an antibody reactive with the CD5 T cell surface antigen is cross-linked to an antibody reactive with a second T cell surface antigen, such as CD4, CD6 or CD8 to enhance lymphocyte activation and function. In an additional preferred embodiment, an antibody reactive with the CD45 family of antigens is cross-linked with an antibody reactive with a second T cell surface antigen such as CD2, CD3, CD5 or CD28 to inhibit lymphocyte activation and function. In yet another preferred embodiment, an antibody reactive with the CD4 antigen is cross-linked with an antibody reactive with CD45 antigen to enhance lymphocyte activation and function.

The invention also relates to novel bispecific antibodies, preferably bispecific monoclonal antibodies comprised of a first binding region reactive with a lymphocyte antigen and a second binding region reactive with a second lymphocyte antigen. In a preferred embodiment, a bispecific monoclonal antibody is prepared having a first binding region reactive with the CD3 antigen and a second binding region reactive with a second lymphocyte antigen such as CD2, CD4, CD6 or CD8 to enhance activation and function of T cells. According to another preferred embodiment, a bispecific monoclonal antibody has a first binding region reactive with the CD5 antigen, and a second binding region reactive with a second lymphocyte antigen such as CD4, CD6, or CD8 to enhance lymphocyte activation and function. In an additional preferred embodiment, a bispecific monoclonal antibody has a first binding region reactive with the CD45 family of antigens and a second binding region reactive with a second lymphocyte surface antigen such as CD2, CD3, CD5 or CD28 to inhibit lymphocyte activation and function.

The antibody heteroconjugates, bispecific antibodies, and methods and compositions of this invention are useful in the regulation of lymphocytes leading to improved cellular immune responses in the treatment of diseases such as infectious disease, cancer, AIDS and autoimmune disease.

BACKGROUND OF THE INVENTION

T lymphocytes, also referred to in the art as T cells, are known to mediate immune responses in at least two distinct ways. Cytotoxic T cells are involved in the lysis of specific target cells, while helper T cells assist in the proliferation and differentiation of B cells, leading to the production of antigen-specific antibodies [see, e.g., Kimball (ed.), *Introduction To Immunology*, 2nd Ed., Chapters 11–13, Macmillan Publishing Co. (1986)]. Either type of T cell is activated to perform its function via the interaction of the T cell receptor (Ti) or its associated CD3 complex (also referred to as the CD3/Ti receptor complex) on the T cell surface with an antigen on an antigen-presenting cell [see, e.g., Reinherz et al., "Clonotypic Surface Structure On Human T Lymphocytes: Functional And Biochemical Analysis Of The Antigen Receptor Complex", *Immunol. Rev.*, 81:95–129 (1984)].

It has been found, however, that T cells respond to an antigen only when that antigen is associated with a particular MHC (major histocompatibility complex)-encoded antigen on the antigen-presenting cell. T cell recognition of an antigen is said therefore to be restricted by the class of MHC-encoded product associated with the antigen. The result of this MHC restriction is that cytotoxic T cells are activated by antigens in association with class I MHC antigens and helper T cells are activated by antigens associated with class II MHC antigens [see, e.g., Kimball (ed.), Introduction To Immunology, supra at pp. 286–89 and pp. 348–58].

Furthermore, it has been recognized that the class II MHC-restricted T cells express, in addition to the CD3/Ti receptor complex, a cell surface antigen termed CD4, whereas the class I MHC-restricted T cells express a CD8 cell surface antigen. This association between MHC restriction and CD antigen expression has led to the hypothesis that, in T cell activation, the respective MHC antigens are the natural ligands for the CD antigens, i.e., the CD4 antigen on helper T cells interacts with the class II MHC molecules on the antigen-presenting cells (e.g., macrophage) and the CD8 antigen on cytotoxic T cells interacts with the class I MHC molecules on specific target cells (e.g., virus-infected cells) [see, e.g., Emmrich et al., "Cross-Linking Of The T Cell Receptor Complex With The Subset-Specific Differentiation Antigen Stimulates Interleukin 2 Receptor Expression In Human CD4 And CD8 T Cells", *Eur. J. Immunol.*, 17:529–34 (1987)]. In addition, it has been proposed that the recognition of antigen by T cells may occur via a quaternary complex wherein the CD3/Ti receptor complex on the T cell surface, in association with a CD antigen such as CD4 or CD8, "sees" the antigen in association with the appropriate MHC-encoded antigen [see, e.g., Anderson et al., "Cross-Linking Of T3 (CD3) With T4 (CD4) Enhances The Proliferation Of Resting T Lymphocytes", *J. Immunol.*, 139 (No. 3):678–82 (1987)].

As used in this application, CD antigens are naturally-occurring cell surface differentiation antigens defined by the reactivity of monoclonal antibodies (mAbs) on the surface of cells, as designated by an International Workshop whose function is to provide a unified nomenclature for these antigens [see, e.g., McMichael (ed.), *Leukocyte Typing III*, Oxford University Press (Oxford, U.K. 1987)]. A large number of CD antigens have been molecularly cloned and are therefore fully characterized [Id.]. Well known CD antigens include the pan-T antigens, CD3, CD2, CD5, CD6 and CD7, a CD antigen specific for the helper T cell subset, CD4, and a CD antigen specific for the suppressor T cell subset, CD8 [see, e.g., Ledbetter et al., in *Perspectives In Immunogenetics And Histocompatibility*, Vol. 6, E. Heise (ed.), Lymphocyte Surface Antigens 1984, pp. 325–40, American Society For Histocompatibility And Immunogenetics (New York 1984)]. CD28 is an antigen present on a majority of T cells [Yamada et al., *Eur. J. Immunol.* 15:1164–1169 (1985)]. Although these differentiation antigens are thought to function as receptors as described above and have been linked to signal transduction in T cells, their exact function in T cell activation is not known and is the subject of intense research.

For example, studies have been carried out to determine the role of CD antigens in T cell activation on a molecular level. It is known that the reaction of an CD3/Ti receptor complex with either mAb or antigen leads to the generation of a transmembrane "signal" within the T cell. This signal is often characterized by the production of inositol monophosphate, bisphosphate and trisphosphate, and an increase in the concentration of cytoplasmic free calcium ($[Ca^{2+}]_i$) [see, e.g., Imboden et al., "Transmembrane Signalling By The T Cell Antigen Receptor", *J. Exp. Med.*, 161:446–56 (1985) and Imboden et al., "Antigen Recognition By A Human T Cell Clone Leads To Increases In Inositol Triphosphate", *J. Immunol.*, 103 (No. 5):1322–24 (1987)].

The generation of this signal may not be sufficient, however, to stimulate the T cell to proliferate [Id. at 873]. Under experimental conditions, when the CD3 T cell surface antigen is cross-linked, e.g., by reacting the cell with a cross-linked antibody, the antibody having been cross-linked either in the presence of accessory cells (e.g., by the interaction of the monocyte Fc receptor with the Fc portion of an antibody to CD3) or by immobilization of the antibody on a solid support, T cell proliferation results.

Thus, mAbs to the CD3/Ti receptor complex that have been coupled to a solid support stimulate T cells to proliferate [see, e.g. Anderson et al., supra and Walker et al., "Activation Of T Cells By Cross-Linking An Anti-CD3 Antibody With A Second Anti-T Cell Antibody: Mechanism And Subset-Specific Activation", *Eur. J. Immunol.*, 17:873–80 (1987)], in part due to the cross-linking of the CD3 antigen and in part due to the prevention of internalization of the CD3/Ti receptor complex, because internalization tends to inhibit T cell activation [see, e.g., Ledbetter et al., "Valency Of CD3 Binding And Internalization Of The CD3 Cell-Surface Complex Control T Cell Responses To Second Signals", *J. Immunol.*, 136:3945–52 (1986)]. There are, however, substantial difficulties with the use of an anti-CD3 immobilized on a solid support to enhance T cell activation in vivo for therapeutic applications. Such a use would involve injection of the solid support, usually small beads, into a patient which would entail certain dangers to the health of the patient, such as blocked or clogged arteries.

Furthermore, it has been proposed that under physiological conditions, even this CD3/Ti stimulation via cross-linking of the CD3 antigen exerts only a minimal signal which may require enhancement by interactions on the T cell surface between CD3/Ti and other CD antigens [see Anderson et al., supra at p.678].

In addition, there is uncertainty as to the exact effect of CD antigen interactions in T cell activation. For example, analysis of spontaneous CD4 loss variants [see Marrack et al., "The Major Histocompatibility Complex Restricted Antigen Receptor On T Cells II. Role Of The L3T4 Product", *J. Exp. Med.*, 158:1077–91 (1983)], as well as gene transfer experiments [see, e.g., Gay et al., "Functional Interaction Between Human T-Cell Protein CD4 And The Major Histocompatibility Complex HLA-DR Antigen", *Nature*, 328:626–29 (1987)], suggest that the expression of CD4 augments T cell responses to specific antigen and that CD4 plays a particularly important role when concentrations of antigens are suboptimal or when the avidity of the T cell for antigen/MHC-encoded antigen is low [see, Regnier-Bigouroux et al., "Accessory Molecules And T Cell Activation I. Antigen Receptor Avidity Differentially Influences T Cell Sensitivity To Inhibition By Monoclonal Antibodies To LFA-1 And L3T4 ", *Eur. J. Immunol.*, 16:1385–90 (1986) and Shaw et al., "Susceptibility Of Cytotoxic T Lymphocyte (CTL) Clones To Inhibition By Anti-T3 And Anti-T4 (But Not Anti-LFA-1) Monoclonal Antibodies Varies With The 'Avidity' Of CTL-Target Interaction", *J. Immunol.*, 134 (No. 5):3019–26 (1985)]. Furthermore, when mAbs reactive with CD3 and CD4 were immobilized on the same solid support, proliferation of T cells exposed to the immobilized antibodies was enhanced. Similarly, when mAbs to CD3 and CD8 were coupled to a solid support, proliferation of T cells was enhanced over that observed upon exposure to antibody to immobilized CD3 alone [see, Anderson et al., supra.]

However, studies with soluble CD4 monoclonal antibody indicate that the soluble antibody inhibits T cell responses, suggesting that CD4 may transmit a negative signal that inhibits T cell activation [see, e.g., Bank et al.,*J. Exp. Med.*, 163:1294 (1985); Tite et al., "The Role Of L3T4 In T Cell Activation: L3T4 May Be Both An Ia-Binding Protein And A Receptor That Transduces A Negative Signal", *J. Cell. Mol. Immunol.*, 2:179–90 (1986); and Rosoff et al., "The Role Of The L3T4 Molecule In Mitogen And Antigen-Activated Signal Transduction", *Cell,* 49:845–53 (1987)].

B lymphocytes, also known as B cells, are the precursors of antibody-producing (plasma) cells. When B cells are stimulated by an antigen, requiring the cooperation of helper T cells and macrophages, the B cells proliferate and differentiate into plasma cells and memory B cells. CD antigens that have been identified on B cells include CD19, CD20, CDw4O, CD45, CD45R and Bgp95 (an antigen that has not yet received a CD designation) [McMichael, *Leukocyte Typing III, supra*].

Another CD antigen of interest is the CD45 leukocyte common antigen (L-CA, also known as T200 or Ly-51. CD45 encompasses a family of major glycoproteins ranging from a molecular weight (Mr) of 180 to 220 kDa that is restricted to cells of hematopoietic lineages [Trowbridge "et al., *Proc. Nat'l. Acad. Sci. USA* 72:157–161 (1975); Komuro et al., *Immunogenetics* 1:452–456 (1975); Schied et al., *Immunogenetics* 9:423–433 (1979) Dalchau et al., *Eur. J. Immunol.* 10:737–744 (1980); and Omary et al., *J. Exp. Med.* 152:842–852 (1980)]. Distinct isoforms of CD45 arise from alternative mRNA splicing. These isoforms are differentially expressed on subpopulations of T and B lymphocytes. Some monoclonal antibodies (mAbs) to human CD45 antigen recognize epitopes shared by all CD45 isoforms of Mr 220, 205, 190 and 180 kDa. [Cobbold et al., *Leukocyte Typing III*, supra, Chap. 15, pp 788–803). However, other mAbs recognize only the 220 kDa isoform of CD45, designated CD45R, that is selectively expressed on B lymphocytes and a subpopulation of T cells. [Cobbold, supra; Dalchau et al.,*J. Exp. Med.,* 153:753–765 (1981); Morimoto et al., *J. Immunol.* 134:1508–1515 (1985); and Ledbetter et al., *J. Immunol.* 135:1819–1825 (1985)]. Another mAb, UCHL-1, selectively binds to the 180 kDa species, which is restricted to cortical thymocytes and a subset of activated or memory T cells. [Smith et al., *Immunology* 58:63–70 (1986)].

Recently, the primary structures of rat [Thomas et al., *Cell*, 41:83–93 (1985) and Barclay, et al., *EMBO J.* 6:1259–1264 (1987)], mouse [Saga, et al., *Proc. Natl. Acad. Sci. USA* 83:6940–6944 (1986); W. C. Raschke, *Proc. Natl. Acad. Sci. USA* 84:161–165 (1987); Thomas et al. *Proc. Natl. Acad. Sci. USA* 84:5360–5363 (1987) and Saga et al., *Proc. Natl. Acad. Sci. USA* 84:5364–5368 (1987)], and human [Ralph et al., *EMBO J.* 6:1251–1257 (1987) and Streuli et al., *J. Exp. Med.* 166:1548–1566 (1987)] CD45 (L-CA) have been deduced from CDNA nucleotide sequences. CD45 is an integral membrane protein with a large 705–707 amino acid cytoplasmic segment, a 22 amino acid trans-membrane segment, and an extracellular domain ranging from 400 to 550 amino acids. The various isoforms of CD45 that are generated by alternative mRNA splicing of primary transcripts of a single gene have different extracellular domains, but have the same transmembrane and cytoplasmic segments [Barclay, supra; Ralph, supra and Streuli, supra]. The cytoplasmic segment has two homologous, highly conserved domains of approximately 300 residues.

Studies attempting to define the function of CD45 have yielded conflicting results [Cobbold, suDra]. mAbs to the human or mouse antigen have been reported to inhibit T and B cell proliferation [Harp et al., *J. Immunol.* 133:10–15 (1984); Bernabeu, et al., *Eur. J. Immunol.* 17:1461–1466 (1987) and Mittler et al., *J. Immunol.* 138:3159–3166 (1987)], cellular differentiation [Yakura, *J. Exp. Med.* 157:1077–1088 (1983)], and natural killer (NK) cell and cytotoxic T cell activity [Seaman et al., *J. Immunol.* 127:982–986 (1981); Newman, *Proc. Nat'l. Acad. Sci. USA* 79:3858–3862 (1982); Nakayama et al., *Proc. Nat'l. Acad. Sci. USA* 76:1977–1981 (1979) and Lefrancois et al., *Nature* (London) 314:449–452 (1985)]. However, under certain conditions, anti-CD45 mAbs have also been reported to augment T cell proliferation [Cobbold, supra; Ledbetter, supra and Martorell, et al., *Eur. J. Immunol.* 17:1447–1451 (1987)]. Thomas, supra, have suggested that the 80 kDa cytoplasmic portion of the molecule with its two conserved homologous domains may play a critical role in CD45 function. Recently, these domains were found to be homologous to a major low-molecular weight protein tyrosine phosphatase isolated from both the soluble and particulate fractions of human placenta [Tonks, et al., *J. Biol. Chem.*, 263:6722–6730 (1988); and Charbonneau et al., *Proc. Nat'l. Acad. Sci. USA* 85:7182–7186 (1988)]. This suggests that CD45 is a membrane-bound protein tyrosine phosphatase which may function by interacting with other membrane-associated molecules.

In the present invention, the antibody heteroconjugates may be presented to react with antigens on lymphocytes to regulate lymphocyte activity. Alternatively, bispecific antibodies, i.e. antibodies containing binding regions reactive with two different cell surface CD antigens may be used to regulate lymphocyte activity.

SUMMARY OF THE INVENTION

The present invention clarifies some of the uncertainties discussed above and provides novel antibody heteroconjugates and bispecific antibodies. The antibody heteroconjugates are comprised of at least two antibodies reactive with different surface antigens expressed on lymphocytes, such as T cells, the antibodies being cross-linked to each other. Certain of these heteroconjugates enhance signal transduction in the activation of T cells as determined by their ability to increase the concentration of intracellular free calcium ($[Ca^{2+}]_i$) in T cells at protein concentrations approximately two orders of magnitude lower than that seen with antibody to the CD3 antigen alone. In addition, the heteroconjugates of the invention include those capable of inhibiting activation and function of lymphocytes.

According to a preferred embodiment of the invention, a monoclonal antibody reactive with the CD3/Ti receptor complex or its component parts is cross-linked to a monoclonal antibody reactive with a second antigen on the T cell surface, such as the CD2, CD4, CD6 or CD8 antigen, to form heteroconjugates that enhance signal transduction in the activation of T cells. According to another preferred embodiment, a monoclonal antibody reactive with the CD5 T cell surface antigen is cross-linked to a monoclonal antibody reactive with a second antigen on the T cell surface, such as the CD4, CD6 or CD8 antigens. A particularly preferred embodiment relates to a heteroconjugate comprised of an antibody to CD3 cross-linked to an antibody to CD4.

According to yet another preferred embodiment, a monoclonal antibody reactive with the CD45 T cell surface antigen is cross-linked to a monoclonal antibody reactive with a second antigen on T cell surfaces such as the CD2, CD3, CD5 or CD28 antigen, to form heteroconjugates that inhibit activation and proliferation of lymphocytes. A particularly preferred embodiment relates to a heteroconjugate comprised of an antibody CD3 cross-linked to antibody reactive with CD45 antigen or the isoforms of CD45.

The invention also provides bispecific monoclonal antibodies comprised of a first binding region reactive with a first surface antigen expressed on lymphocytes and a second binding region reactive with a second lymphocyte antigen on the same cell. Some of these bispecific antibodies enhance signal transduction in the activation of T cells, and others inhibit activation and function of lymphocytes. In particular, the combinations of CD3/CD4, CD3/CD8, CD3/CD2, CD5/CD4, and CD5/CD8 enhance T cell activation.

The present invention also encompasses methods of treating lymphocytes with the heteroconjugates and bispecific antibodies of the invention to enhance or inhibit activation of lymphocytes and in the production of cellular immune responses. These products may therefore be used in pharmaceutical compositions such as those comprising a pharmaceutically effective amount of at least one heteroconjugate of the invention and a pharmaceutically acceptable carrier. Thus, the heteroconjugates and bispecific antibodies and methods and compositions of the invention can be used in immunotherapy to enhance or regulate immune responses, for example, in the treatment of infectious diseases, cancer, AIDS and autoimmune diseases.

BRIEF DESCRIPTION OF THE DRAWINGS

FIG. 11 depicts a schematic representation of the ten forms of antibody produced by a hybrid hybridoma, as described in Example 5, infra.

FIG. 13 (A–J) depicts substrates which are phosphorylated on tyrosine in the CD3+ CEM T cell line (i.e. by activation of the appropriate tyrosine kinase(s) during a time-course of 0, 2 and 5 minutes in response to various stimulations including CD3, CD4 and CD8 antibodies used separately (time-courses B, C, D) or as mixtures (CD3 +CD4 mix and CD3+CD8 mix; time-courses E and H) or as hybrid (bispecific) antibodies (CD3/CD4 HYB and CD3/ CD8 HYB; time-courses F and I) or as heteroconjugated antibodies (CD3/CD4 HC and CD3/CD8 HC; time-courses G and J), as described in Example 6, infra.

FIG. 14 (A–F depicts activation of tyrosine kinase(s) by phosphorylation of various substrates on tyrosine, as described in Example 6, infra. Stimulations included CD5 and CD4 antibodies alone(time-course B and F) or as a mixture (CD5+CD4 mix; time-course C) or as a hybrid (bispecific) antibody (CD5/CD4 HYB; time-course D) or as an antibody heteroconjugate (CD5/CD4 HC; time-course E).

FIG. 15 (A–F) depicts activation of tyrosine kinase(s) by phosphorylation of various substrates on tyrosine, as described in Example 6, infra. Stimulations included CD5 and CD8 antibodies alone (time-course B and F) or as a mixture (CD5+CD8 mix; time-course C) or as a hybrid (bispecific) antibody (CD5/CD8 HYB; time-course D) or as an antibody heteroconjugate (CD5/CD8 HC; time-course E).

DETAILED DESCRIPTION OF THE INVENTION

Figure 1:
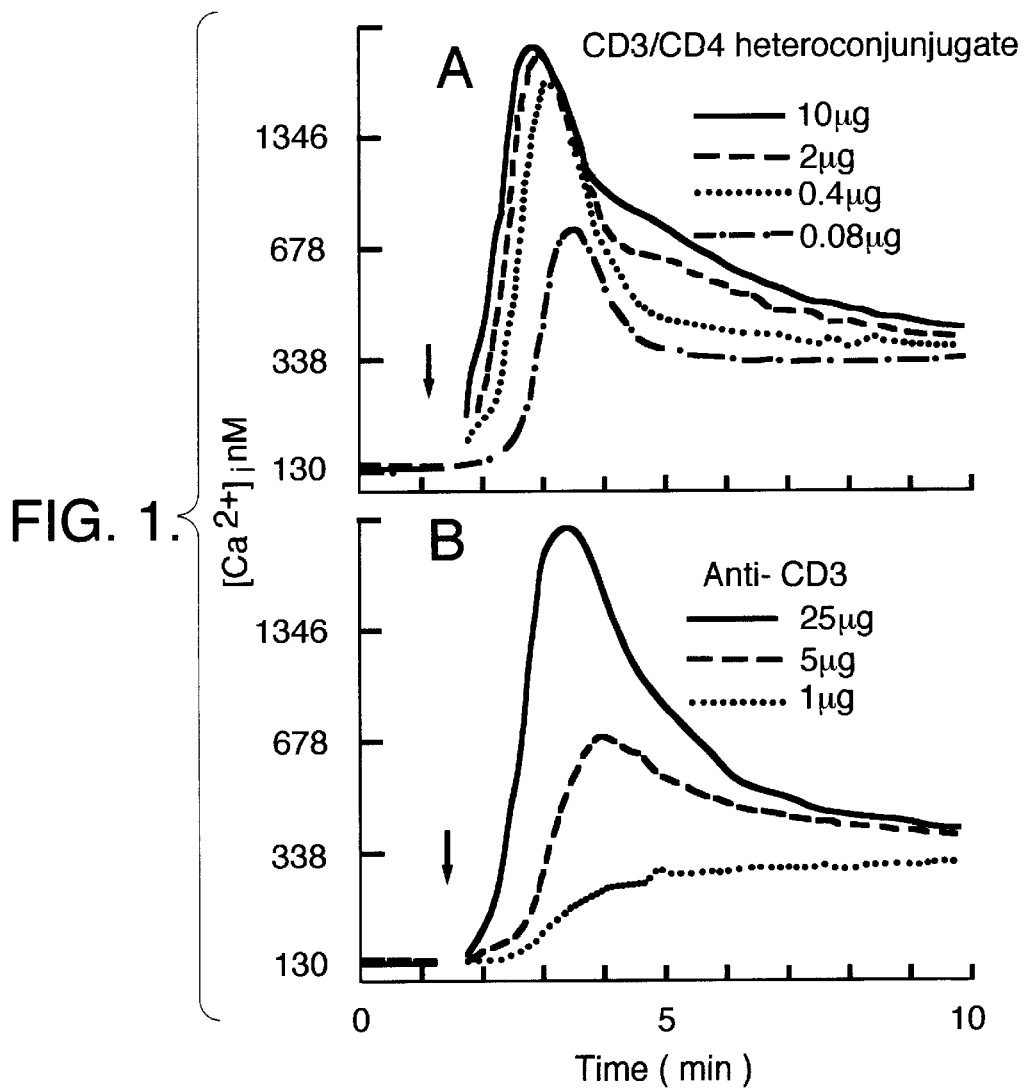
FIG. 1 depicts a comparative graphical presentation of the increase in the concentration of cytoplasmic free calcium ($[Ca^{2+}]_i$) over time upon stimulation of peripheral blood lymphocytes with varying concentrations of either (A) a CD3/CD4 heteroconjugate of one embodiment of the invention, G19-4/G17-2, or (B) the anti-CD3 monoclonal antibody, G19-4.

In order that the invention herein described may be more fully understood, the following detailed description is set forth.

The present invention relates to novel heteroconjugates and bispecific antibodies and their use in the enhancement or inhibition of lymphocyte activation and function. More particularly, the invention relates to heteroconjugates comprised of at least two antibodies cross-linked to each other, each antibody being reactive with a different lymphocyte cell surface antigen. Preferably, for enhancement of lymphocyte activity one of the antibodies of the conjugate is reactive with the T cell receptor (Ti) or its associated CD3 antigen complex and the other antibody is reactive with a second T cell surface antigen, such as the CD antigens (e.g., CD2, CD4, CD6, or CD8). Alternatively, one of the antibodies of the conjugate is reactive with the CD5 antigen and the other antibody is reactive with a second T cell surface antigen such as CD4, CD6 or CD8. The heteroconjugate CD4/CD45 also leads to enhanced T cell activity. For inhibition, one of the antibodies of the heteroconjugates is preferably reactive with the CD45 family of antigens (isoforms), and the other antibody is reactive with a T cell surface antigen such as CD2, CD3, CD5 or CD28.

The bispecific monoclonal antibodies of the invention are comprised of two reactive binding regions, each binding region reactive with a different lymphocyte cell surface antigen. Preferably, for enhancement of lymphocyte activity, one of the binding regions is reactive with the T cell receptor (Ti) or its associated CD3 antigen complex and the other binding region is reactive with a second T cell surface antigen such as the CD antigens (e.g. CD2, CD4, CD6 or CD8). Alternatively, one of the binding regions of the bispecific antibody is reactive with the CD5 antigen and the other binding region is reactive with a second T cell surface antigen such as CD4, CD6 or CD8. For inhibition of lymphocyte activity, one of the binding regions of the bispecific antibody is preferably reactive with one of the CD45 isoforms, and the other binding region is reactive with a T cell surface antigen such as CD2, CD3, CD5 or CD28.

Without being bound by theory, it is believed that the heteroconjugates and bispecific antibodies described herein, when reacted with lymphocytes, act by binding to their respective antigens on the surface of the cell, bringing those antigens into close proximity to each other, a step that may mimic the coclustering that occurs, for example, between the T cell receptor and CD4 upon contact of helper T cells with antigen-presenting cells during T cell activation [see, e.g., Kupfer et al., "Coclustering Of CD4 (L3T4) Molecule With The T-Cell Receptor Is Induced By Specific Direct Interaction Of Helper T Cells And Antigen Presenting Cells", *Proc. Nat'l. Acad. Sci. USA.* 84:5888 (1987)]. This interaction between T cell antigens and the cell surface appears to enhance CD3/Ti-mediated transmembrane signalling and thus T cell activation.

While the mechanism of the CD45 antigen's effect on lymphocytes is not understood, the CD45 heteroconjugates and bispecific antibodies described herein may function by modifying other lymphocyte receptors functionally when brought into close physical association with them, for example resulting in inhibition after aggregation of certain CD receptors, such as the CD3 antigen. The recently described homology between the cytoplasmic domains of CD45 and the major protein tyrosine phosphatase of human placenta suggest that the former is in fact a membrane-bound protein tyrosine phosphatase that functions to modify signal transduction in leukocytes by dephosphorylating key tyrosyl residues on other membrane-associated molecules such as on the zeta chain of CD3. [Klausner et al., *J. Biol. Chem.* 262:12654–12659 (1987)]. CD45 could also modify protein tyrosine kinase activity associated with CD4 that would normally function to regulate antigen-driven signal transduction. [Rudd et al., *Proc. Nat'l. Acad. Sci. USA* 85:5190–5194 (1988)]. Alternatively, the CD4-associated tyrosine kinase may phosphorylate CD45 antigen on its tyrosyl residues and alter its activity. This could account for the unique enhancement activity obtained as a result of cross-linking the CD4 and CD45 receptors as shown in the examples, infra. This model would predict that phosphorylation of key tyrosyl residues precedes and is necessary for the mobilization of calcium. An integral membrane form of the enzyme that functions only in close proximity with other membrane-associated proteins would serve to localize protein tyrosine kinase/phosphatase regulation to specific cell surface molecules. Thus, it is believed that the heteroconjugates and bispecific antibodies of the invention containing regions reactive with two lymphocyte antigens can act to enhance or inhibit lymphocyte activation and function.

It should be noted that the T cell regulation, i.e. inhibition, according to this invention may be a pan-T cell regulation or the regulation of a particular subset or clone of T cells. Pan-T cell regulation results from contacting the T cells with heteroconjugates or bispecific antibodies that regulate the total pool or population of T cells. These heteroconjugates and bispecific antibodies are comprised of antibodies reactive with T cell antigens found on all T lymphocytes. One such heteroconjugate is the CD3/CD2 heteroconjugate of the invention, CD3 and CD2 being pan-T cell antigens [see, e.g., J. A. Ledbetter et al., in *Perspectives In Inmmnogenetics And Histocompatibility*, supra, Table 1].

However, by use of the appropriate heteroconjugate or bispecific antibody, a more specific regulation can be obtained. For example, in cases where it is desired to activate only a specific subpopulation of T cells, such as the helper or suppressor subset, this can be achieved by constructing a heteroconjugate or bispecific antibody wherein one of the antibody binding regions binds to that particular T cell subpopulation, i.e., one region must be reactive with an antigen specific for that subpopulation. The other binding region is preferably specific for a pan-T cell antigen. According to this embodiment then, CD3/CD4 or CD5/CD4 heteroconjugates or bispecific antibodies of the invention specifically enhance the activation of helper T cells (CD4 being specific for the helper T cell subset) while CD3/CD8 or CD5/CD8 heteroconjugates or bispecific antibodies specifically enhance the activation of the suppressor T cell subpopulation (CD8 being specific for the suppressor T cell subset).

Alternatively, a CD3/CD45 heteroconjugate or bispecific antibody specifically inhibits the activation of T cells bearing CD45 antigens. Since isoforms of the CD45 receptor are also expressed on subsets of T cells, the heteroconjugates and bispecific antibodies of the invention that contain a binding region reactive with CD45 isoforms may also be used for regulation of those subsets of T cells.

Finally, where clonotypic regulation is desired, i.e., regulation of specific T cell clones, the heteroconjugates and bispecific antibodies of the invention will contain an anti-clonotypic (Ti) binding region as one of their components, i.e., a region that reacts with the variable region of the T cell receptor of the clone sought to be regulated. Thus, in cases where a clonotypic T cell is unable to adequately see or respond to a particular antigen, e.g., a tumor or viral antigen, or is suppressed in its response, a heteroconjugate or bispecific antibody of this invention comprising an anti-clonotypic binding region specific for that T cell (Ti/CD4, Ti/CD8, Ti/CD6, Ti/CD2) may be used to regulate those T cell clones. Alternatively, for inhibition of a particular clone of T cells, a heteroconjugate or bispecific antibody composed of Ti/CD45 may be used (or Ti/CD45 isoform). According to this embodiment, the Ti component of the heteroconjugate or bispecific antibody can be viewed as essentially taking the place of the antigen in the regulation of the specific T cell. The other binding region of the heteroconjugate or bispecific antibody may be a pan-T cell-specific or subset-specific binding region or a region reactive with CD45 or CD45 isoform.

Thus, the antibodies that comprise the heteroconjugates of the invention include any antibody reactive with a lymphocyte surface antigen. According to a preferred embodiment, one of the antibodies of the conjugate is reactive with the Ti or CD3 T cell antigen. According to a further preferred embodiment, an antibody reactive with the CD3 T cell surface antigen is cross-linked to an antibody reactive with the CD4 antigen on the T cell surface.

Other antibodies that may comprise the heteroconjugates of the invention include, but are not limited to, antibodies reactive with other CD antigens, e.g., CD2, CD5, CD6, CD7, CD8, and CD28 on lymphocytes [see, e.g., Bernard et al. (eds.), *Leukocyte Typing*, Springer Verlag (Heidelberg 1984); and Ledbetter et al., in *Perspectives In Immunogenetics And Histocompatibility*, supra]. Thus, according to another preferred embodiment, an antibody reactive with the CD5 T cell surface antigen is cross-linked to an antibody reactive with the CD4, CD6 or CD8 antigen to form a heteroconjugate of the invention. Yet another preferred embodiment is an antibody reactive with the CD3 T cell surface antigen cross-linked to an antibody reactive with the CD45 antigen or isoform of CD45 on the lymphocyte cell surface.

The antibodies that comprise the heteroconjugates of the invention may be polyclonal or preferably, monoclonal, may be intact antibody molecules or fragments containing the active binding region of the antibody, e.g., Fab or F(ab')2, and can be produced using techniques well established in the art [see, e.g., publications describing the preparation of anti-CD3, anti-CD4, anti-CD5 and anti-CD2 monoclonal antibodies referenced in Examples 1–3 below]. In addition, monoclonal antibodies to many of the CD antigens such as the CD2, CD3, CD4 and CD5 antigens are commercially available (Becton Dickinson, Mountainview, Calif.) or may be obtained from the International Leukocyte Typing Workshops. If monoclonal antibodies are used, the antibodies may be of mouse or human origin or chimeric antibodies [see, e.g., Oi, "Chimeric Antibodies", *BioTechniques.* 4 (No. 3):214–221 (1986)].

The antibodies that comprise the heteroconjugates of this invention can be covalently bound to each other by techniques known in the art such as the use of the heterobifunctional cross-linking reagents, GMBS (maleimidobutryloxy succinimide) or SPDP (N-succinimidyl 3-(2-pyridyldithio) propionate) [see, e.g., Hardy, "Purification And Coupling Of Fluorescent Proteins For Use In Flow Cytometry", *Handbook Of Experimental Immunology*, Volume 1, Immunochemistry, Weir et al. (eds.), pp. 31.4–31.12 4th Ed., (1986) for a discussion of conventional antibody coupling techniques].

It is to be understood, therefore, that the present invention encompasses any heteroconjugate or bispecific antibody comprised of at least two molecules or regions reactive with different lymphocyte antigens on the same lymphocyte, the heteroconjugate or bispecific antibody acting to enhance or inhibit the activation and function of the lymphocyte. The invention contemplates heteroconjugates and bispecific antibodies reactive with antigens on B cells as well as T cells.

It is apparent that in addition to antibodies, the heteroconjugates of the present invention may incorporate ligands capable of binding to lymphocyte receptors. For example, CD4 receptor has been shown to be reactive with the ligand gp120 (a glycoprotein receptor of the Human Immunodeficiency Virus or "HIV") [Linsley et al., *J. Virology* 62:3695–3702 (1988)). Thus, a heteroconjugate consisting of anti-CD3 antibody cross-linked to the ligand gp120would be used to enhance T cell activity by cross-linking the CD3 and CD4 receptors. Other ligand conjugates consisting of a ligand reactive with a T cell receptor cross-linked to a ligand reactive with a different T cell receptor are also contemplated. These could include growth factors such as Interleukin-1 ("IL-1"), IL-2, IL-4, etc.

The heteroconjugates of the invention and their use in T cell activation are exemplified by a preferred embodiment in which an antibody reactive with the CD3 antigen on the surface of T cells was conjugated to an antibody reactive with the CD4 antigen to form a novel CD3/CD4 heteroconjugate of the invention. Treatment of CD4$^+$ T cells with this heteroconjugate resulted in enhanced signal transduction in the helper subset of T cells as indicated by a significant increase in intracellular $[Ca^{2+}]_i$ mobilization and substantial increases in inositol monophosphate, bisphosphate and inositol trisphosphate formation compared with treatment of the cells with antibody to CD3 alone. This signal-enhancing activity of the CD3/CD4 heteroconjugate was not simply due to oligomerization, since CD3/CD3 and CD4/CD4 homoconjugates or mixtures thereof did not show this increased activity. And, it has been previously demonstrated in the art that mixtures of anti-CD3 and anti-CD4 antibodies decrease rather than enhance this activity [see, e.g., Rosoff et al., supra]. Furthermore, the enhanced activity demonstrated by the heteroconjugate was inhibited by pretreatment of the T cells with soluble monoclonal antibody to CD4.

In addition, the CD3/CD4 heteroconjugate exhibited a novel functional activity in T cell activation, i.e., the heteroconjugate induced the proliferation of CD4+ T cells in the presence of a monoclonal antibody reactive with CD28 and was fully comitogenic with CD28 stimulation even at concentrations as low as 100 ng/ml. Such comitogenicity was not found using antibody to CD3 alone or CD3/CD3 or CD4/CD4 homoconjugates. Furthermore, it was found that the CD3/CD4 heteroconjugate of the invention, in combination with CD28 monoclonal antibody, was able to significantly drive the T cells through the cell cycle, with a significant fraction of the cells entering a second cycle within the first three days of stimulation. In contrast, antibody to CD3 alone or CD3/CD3 or CD4/CD4 homoconjugates did not induce significant cell cycle transition.

Additionally, it was found that the CD3/CD4 heteroconjugate caused the modulation of both the CD3 and CD4 antigens on the T cell surface, leading to a decrease in the surface expression of CD4. This result indicates that the heteroconjugate is not simply anchoring the T cell receptor to the T cell surface as was previously shown to be the case using immobilized antibody to CD3 [see, e.g., Ledbetter et al., *J. Immunol.*, supra].

The results obtained with the CD3/CD4 heteroconjugate demonstrate that the CD4 antigen on the T cell surface plays an active positive role in signal transduction during T cell activation of CD4$^+$ helper T cells via a physical interaction between the CD3/Ti receptor complex and the CD4 antigen.

The molecular mechanisms that underlie the CD3/CD4 heteroconjugate's ability to augment signal transduction are not well understood. At least one effect of the CD4 interaction with CD3/Ti appears to be the enhancement of inositol phosphate production, suggesting that CD4 may promote CD3/Ti-induced hydrolysis of membrane phosphoinositides, leading to the production of inositol trisphosphate. This is supported by our experimental data indicating that the inositol phosphate-generating activity of the CD3/CD4 heteroconjugate is inhibited by reaction of the cells with soluble CD4 monoclonal antibody. This inhibition may be a consequence of antibody-induced dissociation of CD4 and CD3/Ti, if CD3/Ti alone is a less efficient signal transducer. Alternatively, independent interaction of CD4 with its antibody may transmit a negative signal that inhibits the generation of inositol phosphates.

Since the generation of inositol trisphosphate (InsP$_3$) is believed to mediate mobilization of cytoplasmic calcium in T cells, the interaction of CD4 with CD3/Ti also appears to promote release of calcium from intracellular stores. Comparison of the dose-response curves of the CD3/CD4 heteroconjugate vs. antibody to CD3 in $[Ca^{2+}]_i$ mobilization indicates that a detectable $[Ca^{2+}]_i$ response is achieved from the interaction of far fewer receptors on the T cell when CD4 and CD3/Ti are stimulated in proximity, i.e., by use of the CD3/CD4 heteroconjugate, than when CD3/Ti is stimulated alone (see FIG. 3). Thus, one property of the CD3/CD4 heteroconjugate of the invention is its ability to activate T cells at low levels of receptor occupancy.

Because it is known that inositol phosphate generation and calcium mobilization are signals associated with the activation of T cells, leading to T cell proliferation, the data presented herein clearly demonstrates that, regardless of the mechanism of action, the CD3/CD4 heteroconjugate of the invention is useful in the enhancement of T cell activation and proliferation.

The present invention also encompasses other heteroconjugates that, like the CD3/CD4 heteroconjugate, display enhanced signalling capabilities in T cell activation. For example, a CD3/CD2 heteroconjugate, a CD3/CD6 heteroconjugate, a CD3/CD7 heteroconjugate and a CD3/CD8 heteroconjugate of the invention also displayed enhanced activity in the mobilization of calcium. Furthermore, according to this invention, several anti-CD5-containing heteroconjugates were also constructed (e.g., a CD5/CD4 heteroconjugate, a CD5/CD6 heteroconjugate and a CD5/CD8 heteroconjugate) and displayed enhanced activity in the mobilization of $[Ca^{2+}]_i$ in T cells.

The heteroconjugates of the invention incorporating an antibody reactive with CD45 antigen or its isoforms and useful for inhibition of lymphocyte activation and function, or enhancement of T cell activation and function, are exemplified by a preferred embodiment in which an antibody reactive with the CD3 antigen was conjugated to an antibody reactive with the CD45 antigen to form a novel CD3/CD45 heteroconjugate of the invention. Treatment of T cells with this heteroconjugate resulted in abrogation of CD3-mediated activation (transmembrane signal) of the T cells as indicated by a significant decrease in intracellular calcium mobilization.

In addition, induction of interaction between various CD receptors on the surface of T cells such as CD3, CD2, CD5 or CD28, and the CD45 receptor was accomplished using monoclonal antibodies to cross-link the CD45 receptor on the lymphocyte with another CD receptor on the same lymphocyte. This cross-linking resulted in abrogation of the increase in $[Ca^{2+}]_i$ that occurred from formation of homo-aggregates of the T cell antigens induced by cross-linking common receptors on the cell surface. T cell proliferation initiated by immobilized anti-CD3 monoclonal antibody stimulation was inhibited by anti-CD45 antibody or anti-CD45R antibody when immobilized on the same surface, but not when in solution. Similarly, proliferation of T cells after stimulation of the CD2 and CD28 receptors by anti-CD2 and anti-CD28 antibodies, respectively, was inhibited when a CD45 antibody was cross-linked to either anti-CD2 antibody or anti-CD28 antibody, but not when an anti-CD45 antibody was bound to the cell surface separately. These results suggest that heteroconjugates consisting of antibodies reactive with CD45 or isoforms of CD45 such as CD45R and antibodies reactive with CD antigens on T cells may be useful to regulate the cells.

In contrast, the increase in $[Ca^{2+}]_i$ induced by formation of homoaggregates of CD4 receptors on T cells was strongly amplified when the CD4 receptor was cross-linked to the CD45 receptor using monoclonal antibodies. Thus, a novel heteroconjugate consisting of antibody against CD4 and antibody reactive with CD45 or isoforms of CD45R on T cells may also be used to enhance T cell function of all CD4 positive cells or subpopulations of CD4 cells defined by expression of CD45 isoforms.

The present invention also encompasses bispecific monoclonal antibodies having one binding region reactive with one lymphocyte antigen and the other binding region reactive with a second antigen on the same cell.

Methods for producing the bispecific antibodies of the invention include fusion of two parental hybridomas, one of which is preselected for sensitivity to HAT medium and the other is poisoned with a lethal dose of iodoacetamide prior to cell fusion. [Clark et al., in "Hybrid Antibodies for therapy", in Monoclonal Antibody Therapy: Prog. Allergy, Waldmann, Ed., 45:31–49 Basel, Karger (1988); and in "T-Cell Killing of Target cells induced by hybrid antibodies: A comparison of two bi-specific monoclonal antibodies", *J. Natl. Cancer Inst.* 79:1393–1401 (1987)]. This method was adapted for use in the present invention as described in greater detail in Example 5, infra. Other methods include production of a quadroma or trioma cell as described in U.S. Pat. No. 4,474,893 or using chemical methods as described by Brennan et al., *Science* 229:81–83 (1985).

The hybrid hybridomas of the invention produced as described in Example 5, infra, and producing the bispecific antibodies of the invention have been deposited with the American Type Culture Collection, "ATCC", in 12301 Parklawn Rockville, Md. 20852 under the Budapest Treaty and have there been identified as follows:

| Hybrid Hybridoma | ATCC Accession No. | Deposit Date |
| --- | --- | --- |
| HFB 75.5 (CD5/CD4) | HB 10325 | January 16, 1990 |
| HFC 80.6 (CD5/CD8) | HB 10326 | January 26, 1990 |

The reactive binding regions that comprise the bispecific antibodies of the invention include those regions reactive with a lymphocyte surface antigen. In a preferred embodiment, one of the binding regions of the bispecific antibody is reactive with the Ti or CD3 T cell antigen. According to a further preferred embodiment, the bispecific antibody contains a first binding region reactive with the CD3 T cell antigen and a second binding region reactive with the CD4 antigen on the T cell surface. Other bispecific monoclonal antibodies of the invention include those containing binding regions reactive with other CD antigens, e.g. CD2, CD5, CD6, CD7, CD8, and CD28 on lymphocytes. Thus, according to another preferred embodiment, a bispecific antibody is produced containing a binding region reactive with the CD5 T cell surface antigen and a binding region reactive with the CD4, CD6 or CD8 antigen. Yet another preferred embodiment is a bispecific antibody containing a binding region reactive with the CD45 antigen or isoform of CD45 antigen (CD45R) on the lymphocyte cell surface for inhibition of lymphocyte activation and function.

As shown in the Examples, infra, the CD3/CD4 bispecific antibody displays enhanced signalling capabilities in T cell activation. CD3/CD8, CD5/CD4 and CD5/CD8 bispecific antibodies also displayed enhanced activity in the mobilization of calcium. In addition, bispecific antibodies of CD3/CD4, CD3/CD8, and CD3/CD2 induced cellular proliferation of resting T cells in the presence of anti-CD28 antibody.

The heteroconjugates and bispecific antibodies of the invention are useful to regulate lymphocytes in vitro or in vivo, and therefore, may be used to regulate cellular immune responses in disease states such as infectious diseases, cancer, AIDS and autoimmune disorders. These heteroconjugates and bispecific antibodies may be especially useful for the regulation of cellular immune responses in disease states where there is a defect or disregulation of T cells.

For example, it has been shown that CD45 isoforms are abnormally expressed in certain autoimmune diseases [Rose et al., *Proc. Natl. Acad. Sci. (USA)* 82:7389–7393 (1985)]. Therefore, heteroconjugates or bispecific antibodies of the invention containing at least one molecule or region reactive with CD45 receptor or CD45 isoforms may be useful in regulating lymphocyte function in autoimmune diseases.

In addition, the heteroconjugates and bispecific antibodies of the present invention may be useful in enhancing immune responsiveness in patients with Acquired Immunodeficiency Syndrome (AIDS). It is known that the CD4 antigen serves as the receptor for the Human Immunodeficiency Virus (HIV) that is responsible for AIDS. It is believed that CD4 is the receptor to which the gp120 envelope glycoprotein of HIV binds during infection of T cells with the virus [see, e.g., Lasky et al., *Cell,* 50:975 (1987) and Kowalski et al., *Science,* 237:1351 (1987)]. After HIV infection, the cell surface expression of CD4 is down regulated and levels of CD4 mRNA are decreased [see Hoxie et al., "Alterations In T4 (CD4) Protein And mRNA Synthesis In Cells Infected With HIV", *Science,* 234:1123–1127 (1986)]. It is also well established that AIDS patients display reduced immune responsiveness to soluble antigens [see, e.g., Lane et al., "Qualitative Analysis Of Immune Function In Patients With The Acquired Immunodeficiency Syndrome", *New Eng. J. Med.,* 313 (No. 2):79–84 (1985)]. In vitro studies have shown that purified HIV gp120 can inhibit T cell responses to mitogenic stimulation, a result similar to the effect we have seen using soluble monoclonal antibody to CD4 [see Mann et al., *J. Immunol.,* "HTLV-III Large Envelope Protein (gp120) Suppresses PHA-Induced Lymphocyte Blastogenesis", 138:2640–2644 (1987)].

Thus, it may be proposed that the immunosuppression seen in AIDS patients may be related to the effect of HIV infection on CD4 antigen expression, i.e., the down regulation of CD4 on the T cell that occurs after HIV infection may affect immune responsiveness by diminishing the signalling capability of the cell, leading to decreased T cell activation in response to antigen. In support of this model, we have found that CD3-stimulated increases in free calcium concentration are impaired in HIV-infected cells [Linette et al., "HIV-1 Infected T Cells Exhibit A Selective Transmembrane Signalling Defect Through The CD3/Antigen Receptor Pathway", *Science,* 241:573–576 (1988)]. These observations suggest that the heteroconjugates and bispecific antibodies of the invention, particularly a CD3/CD4 heteroconjugate or bispecific antibody, may be useful for studying or treating T cell dysfunctions resulting from HIV infection.

The heteroconjugates or bispecific antibodies can also be utilized in the in vitro activation of T cells. This activation can be carried out by contacting T lymphocytes taken from a patient with at least one of the heteroconjugates or bispecific antibodies of this invention in vitro whereby the T cells become activated and can then be reinfused into the autologous donor [see, e.g., Rosenberg et al., "Immunotherapy Of Cancer By Systemic Administration Of Lymphoid Cells Plus Interleukin 2", *J. Biol. Resp. Modif.,* 3:5501–5511 (1984)]. This method of treatment may also involve the in vitro co-incubation or preincubation of the T cells with other immunomodulators. According to an alternative embodiment, the heteroconjugates or bispecific antibodies may be used to activate T cells in vivo by injecting them into a patient, possibly in conjunction with other agents such as interleukin-2 (IL-2), growth factors or agonistic antibodies such as CD5 [see, e.g., Clark et al., "Amplification Of The Immune Response By Agonistic Antibodies", *Immunology Today,* 7:267–270 (1986)] and CD28 (see Example 1 below). Regardless of the method of treatment, heteroconjugates comprising antibody fragments such as Fab or F(ab')$_2$, or chimeric antibodies, or the bispecific antibodies of the invention may be preferred for in vivo administration because they are smaller in size and/or lack functional Fc-binding domains and therefore are not as easily removed from the body by the reticuloendothelial system (RES) as are intact heteroconjugates.

The heteroconjugates or bispecific antibodies of the invention can also be administered in vivo using conventional modes of administration which include, but are not limited to, intravenous, oral, subcutaneous, intraperitoneal or intralymphatic. Intravenous administration is preferred.

The pharmaceutical compositions of the invention comprising the heteroconjugates or bispecific antibodies may be in a variety of dosage forms which include, but are not limited to, solid, semi-solid and liquid dosage forms such as tablets, pills, powders, liquid solutions or suspensions, suppositories, polymeric microcapsules or microvesicles, liposomes, and injectable or infusible solutions. The preferred form depends upon the mode of administration and the therapeutic application.

The heteroconjugate or bispecific antibody compositions may include conventional pharmaceutically acceptable carriers known in the art such as serum proteins such as human serum albumin, buffer substances such as phosphates, water or salts or electrolytes.

The most effective mode of administration and dosage regimen for the compositions of this invention depends upon the severity and course of the disease, the patient's health and response to treatment and the judgment of the treating physician. Accordingly, the dosages of the heteroconjugates or bispecific antibodies should be titrated to the individual patient. Nevertheless, an effective dose of heteroconjugate of this invention may be in the range of from about 1 to about 100 mg/m$^2$. For in vitro treatment of T cells, a dose of from about 200 µg to 2 mg of heteroconjugate/$10^9$ cells may be used.

In addition, the heteroconjugates and bispecific antibodies of the invention may be used diagnostically to measure the receptor function of a given T cell surface antigen, e.g., CD antigen, in patients having diseases involving a defect or disregulation of T cells. Using a calcium assay as described herein for the measurement of signal transduction (see Example 1) and appropriate controls, one can measure a defect in CD function by comparing the activation, by a specific heteroconjugate or bispecific antibody of the invention, of T cells from a normal vs. a diseased donor. For example, the CD3/CD4 heteroconjugate of this invention enhances $(Ca^{2+})_i$ mobilization at protein concentrations below that seen with soluble anti-CD3 alone. Thus, at these low doses, one is actually measuring the function of the CD4 receptor. This is reflected by the ability of soluble anti-CD4 to block the activity of the CD3/CD4 heteroconjugate at these doses (see FIG. 2). Similarly, with the CD3/CD8 heteroconjugate at low doses, one is able to measure the function of the CD8 receptor. At low doses then, a heteroconjugate or bispecific antibody can be used to detect defects in a particular CD receptor function in various disease states, such as cancer and autoimmune disease. Alternatively, the calcium assays can be run at any dose with any heteroconjugate or bispecific antibody of the invention as long as the appropriate single antibody controls are carried out, i.e., the activity of the heteroconjugate or bispecific antibody of the invention must be compared to the activity of the unconjugated antibodies that make up the components of that heteroconjugate or bispecific antibody [see, e.g., European Patent Application 221,768 of Reinherz et al., published on May 13, 1987].

In order that the invention described herein may be more fully understood, the following examples are set forth.

It should be understood that the examples are for illustrative purposes only and are not to be construed as limiting the scope of this invention in any manner.

EXAMPLE 1

The following example describes the preparation and characterization of a novel heteroconjugate of the invention. According to this embodiment, an antibody reactive with CD3 was cross-linked to an antibody reactive with CD4 to form a novel CD3/CD4 heteroconjugate that causes enhanced transmembrane signalling in the activation of CD4$^+$ (i.e., helper) T cells treated with the heteroconjugate.
Preparation of A CD3/CD4 Heteroconjugate of The Invention The CD3 and CD4 antibodies utilized to form the heteroconjugate of this embodiment were G19-4 (Balb/c, IgG$_1$) and G17-2 (Balb/c, IgG$_1$), respectively. These antibodies were prepared as described by Ledbetter and Clark, "Surface Phenotype And Function Of Tonsillar Germinal Center Mantle Zone B Cell Subsets", *Human Immunology*, 15:30–43 (1986) and Ledbetter et al., "An Immunoglobulin Light Chain Dimer With CD4 Antigen Specificity", *Molecular Immunology*, 24 (No. 12):1255–1261 (1987). In addition, other anti-CD3 and anti-CD4 monoclonal antibodies that can be used to construct the heteroconjugate of this embodiment are commercially available (e.g., T3, Coulter Co., FL and Leu-3, Becton Dickinson, Calif., respectively). The G19-4 and G17-2 antibodies were purified from ascites fluid by salt precipitation and DEAE chromatography, followed by dialysis and filtration through 0.45μ filters prior to use.

The two monoclonal antibodies were conjugated at a 1:1 molar ratio with the heterobifunctional cross-linking reagent, GMBS (Calbiochem, La Jolla, Calif.) and 5-iminothiolane HCl (Pierce Chemical Co., Rockford, Ill.) as described for phycoerythrin coupling by Hardy, supra. The heteroconjugate that resulted was separated from free antibody by Superose 6 (Pharmacia, Uppsala, Sweden) FPLC size exclusion chromatography and tested for reactivity with both CD3 and CD4 by testing the ability of the heteroconjugate to block the binding of directly fluorescein-conjugated anti-CD3 and anti-CD4 monoclonal antibodies. This CD3/CD4 heteroconjugate was designated G19-4/G17-2.
Enhanced Calcium Mobilization By The CD3/CD4 Heteroconjugate Of The Invention The G19-4/G17-2 heteroconjugate was then tested for its ability to enhance the mobilization of cytoplasmic calcium in cells, compared to the activity of G19-4 (anti-CD3) alone. The cells used were human peripheral blood by lymphocytes purified from the peripheral blood centrifugation on Ficoll-Hypaque, followed by adherence to plastic to remove the majority of monocytes.

Increases in [Ca$^2$+]$_i$ within the cells were measured using indo-l (Molecular Probes, Eugene, Oreg.) and a model 50 HH/2150 flow cytometer (Ortho Diagnostic Systems, Inc., Westwood, Mass.) as described previously by Rabinovitch et al., "Heterogeneity Among T Cells In Intracellular Free Calcium Responses After Mitogen Stimulation With PHA or Anti-CD3.

Simultaneous Use Of Indo-1 And Immunofluorescence With Flow Cytometry", *J. Immunol.*, 137(No. 3): 952–961 (1986), incorporated by reference herein. Briefly, cells (5×10$^7$ ml) were loaded with indo-1 by incubation with its acetoxy-methyl ester (Molecular Probes, Junction City, Oreg.) which is permeable through the cell membrane and is hydrolyzed in the cytoplasm to the impermeant trapped form. The incubation was carried out for 45 min at 37° C. in medium containing the indicated indo-1 concentration. Cells were then washed and resuspended in fresh medium at 2.5×10$^6$/ml and stored in the dark at room temperature until analysis. For each assay, indo-1-loaded cells were diluted to 1×10$^6$/ml with medium and equilibrated at 37° C. Measurements were performed using spectrofluorimetry and flow cytometry as described by Rabinovitch, supra. The histograms were analyzed by programs that calculated the mean indo-1 violet/blue fluorescence ratio vs. time. In addition, the percentage of responding cells vs. time was analyzed by programs that first determined the value of the indo-1 ratio that was two standard deviations about the ratio for control cells and then plotted the percentage of cells above this threshold value vs. time. There are 100 data points on the X (time) axis on all flow cytometric data.

As shown in FIG. 1, the concentration of G19-4/G17-2 required to increase the concentration of Ca$^{2+}$ ([Ca$^{2+}$]$_i$ was 1.5 to 2 orders of magnitude lower than the concentration required using G19-4 alone. Furthermore, the activity of the G19-4/G17-2 heteroconjugate was restricted to CD4$^+$ T cells, since enrichment for CD4$^+$ cells by immunofluorescence resulted in a corresponding increase in [Ca$^{2+}$]$_i$ activity and percent of responding cells. Thus, as FIG. 2 demonstrates, when peripheral blood lymphocytes were stimulated by the G19-4/G17-2 response for heteroconjugate, the mean maximal (Ca$^{2+}$]$_i$ response for the cells was approximately 1300 nM and approximately 60% of the cells responded. However, when only the CD4$^+$ subset of cells was analyzed, the mean maximal [Ca$^{2+}$]$_i$ response was >10,000 nM and >95% of the cells responded. Furthermore, the activity of the heteroconjugate on CD4$^+$ cells was almost completely inhibited by pretreatment of the cells at −5 min with 5 μg/ml G17-2 (anti-CD4) followed by 0.4 μg/ml of the heteroconjugate.

Figure 2:
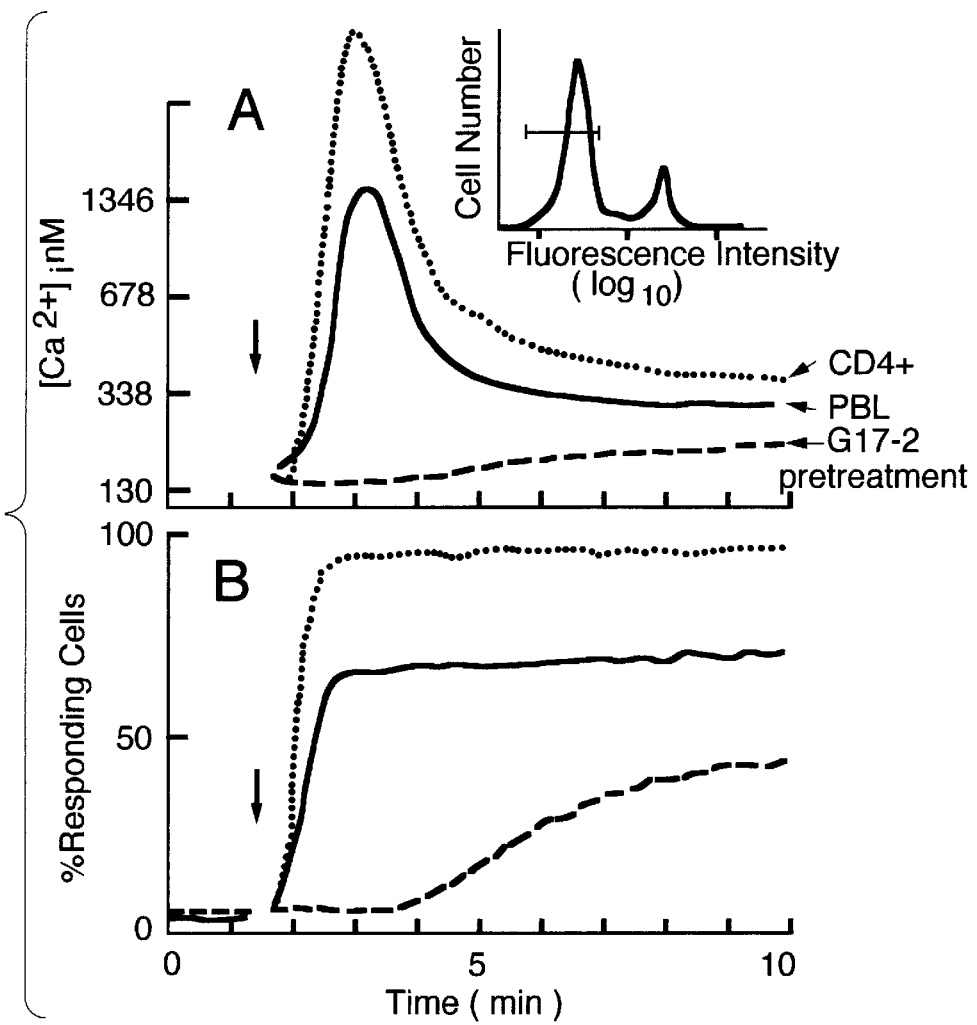
FIG. 2 depicts comparative graphical presentations of the $[Ca^{2+}]_i$ response and percentage of responding cells over time upon stimulation of either unseparated peripheral blood lymphocytes (PBLs) or CD4+ T cells with a CD3/CD4 heteroconjugate of the invention, G19-4/G17-2. The inhibitory effect of pretreatment of the cells with the anti-CD4 monoclonal antibody, G17-2, followed by stimulation with the heteroconjugate is also shown.

The CD4$^+$ cells were analyzed by gating on CD8 negative, CDll negative, CD16 negative and CD20 negative cells as shown in the panel insert of FIG. 2. This negative selection for CD4$^+$ cells was carried out by staining peripheral blood lymphocytes with phycoerythrin (PE)-conjugated 2H7, a monoclonal antibody reactive with CD20 [see, e.g. Clark et al., "Role Of The Bp35 Cell Surface Polypeptide In Human B-Cell Activation", *Proc. Natl. Acad. Sci. USA*, 82:1766–1770 (1985)], FC-2, a monoclonal antibody to CD16 [see, e.g., Anasetti et al., "Induction Of Calcium Flux And Enhancement Of Cytolytic Activity In Natural Killer Cells By Cross-Linking Of The Sheep Erythrocyte Binding Protein (CD2) And The Fc-Receptor (CD16)", *J. Immunol.*, 139 (No. 6):1772–1779 (1987)], G10-1, a monoclonal antibody to CD8 ] [see, e.g., Ledbetter et al., "Covalent Association Between Human Thymus Leukemia-Like Antigens And CD8 Molecules", *J. Immunol.*, 134:4250–4254 (1985)], and 60.1, a monoclonal antibody reactive with CD11 [see, e.g., J. P. Bunyon et al., "Differential Participation Of Epitopes On Alpha And Beta Chains Of The LFA Family In Neutrophil Aggregation As Defined By Workshop Monoclonal Antibodies", in *Leukocyte Typing III*, supra, pp. 844–47], and gating on the unstained cells, which were >95% CD4 positive.

Figure 3:
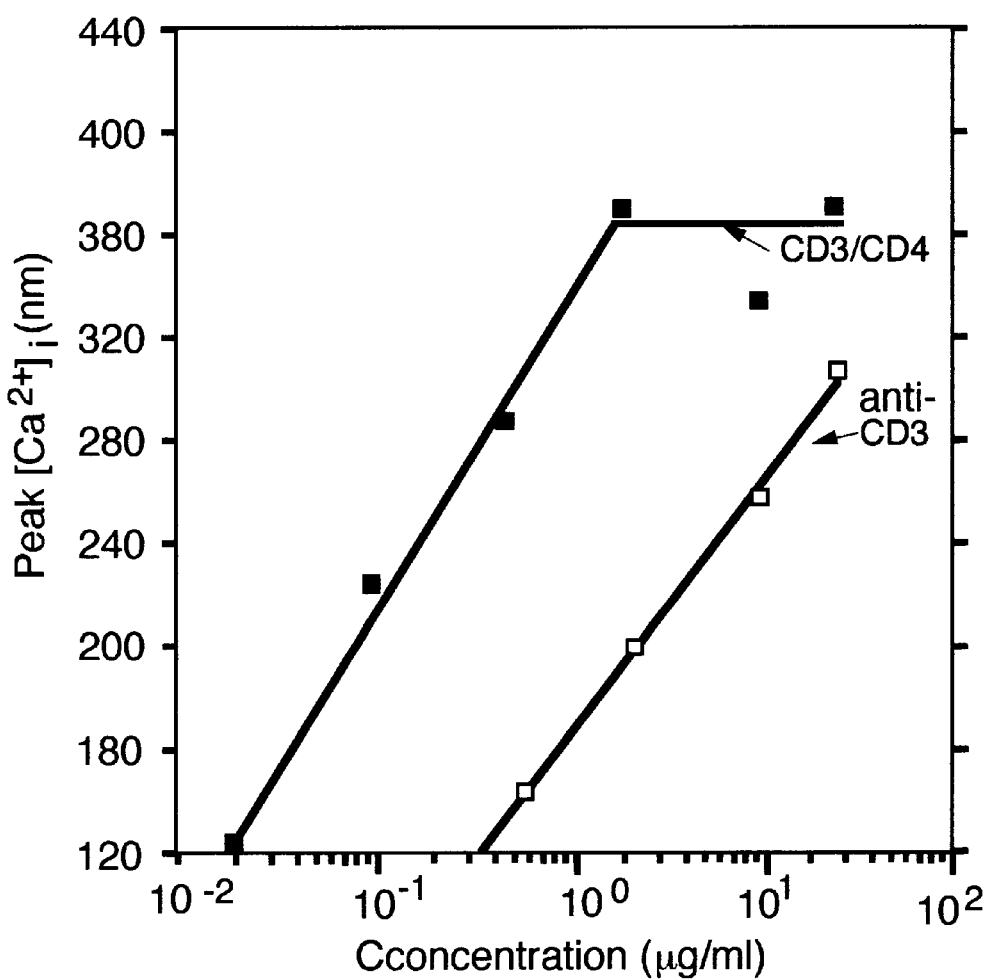
FIG. 3 depicts comparative titrations of the $[Ca^{2+}]_i$ activity of the G19-4/G17-2 heteroconjugate of the invention (■) or the anti-CD3 monoclonal antibody, G19-4 (☐), on $CD^{4+}$ T cells in the presence of 5 mM EGTA.

Comparative titrations of G19-4 vs. the G19-4/G17-2 heteroconjugate were also carried out in the presence of 5 mM EGTA [ethylene glycol-bis (B-aminoethyl ether)-N,N, N',N'-tetraacetic acid], which chelates and thus removes extracellular calcium, to see if it was calcium mobilization from cytoplasmic sources that was being affected by the heteroconjugate. FIG. 3 shows that there was approximately a two log increase in ability to mobilize calcium with the G19-4/G17-2 heteroconjugate in the presence of EGTA. In the presence of extracellular calcium, titrations to the end point indicated an approximately two-log increase in activity as well (data not shown).

In order to exclude that valency of binding to the CD3 or CD4 antigens was responsible for the effects of the CD3/CD4 heteroconjugate on $[Ca^{2+}]_i$, we constructed CD3/CD3 and CD4/CD4 homoconjugates to compare with the CD3/CD4 heteroconjugate. The homoconjugates were constructed as described above for the CD3/CD4 heteroconjugate and have been designated G19-4/G19-4 and G17-2/G17-2, respectively. As shown in Table 1 below, neither the CD3/CD3 homoconjugate nor the mixture of CD3/CD3 plus CD4/CD4 homoconjugates mimicked the enhanced effects of the CD3/CD4 heteroconjugate on $[Ca^{2+}]_i$. This data suggests that the enhanced activity of the CD3/CD4 heteroconjugate is not a function of the valency of the heteroconjugate and therefore presumably results from the physical proximity of the CD3 and CD4 molecules that occurs via interaction of those antigens with the heteroconjugate. Furthermore, heteroconjugates and homoconjugates were slightly less active than free antibodies in binding assays using indirect staining and flow cytometry (data not shown). Thus, the unique activity of the CD3/CD4 heteroconjugate is unlikely to be related to an effect on CD3 binding affinity contributed by the second specificity of the heteroconjugate.

TABLE I

CD4+ T Cell $[Ca^{2+}]i$ Response to CD3/CD4 Heteroconjugate Versus CD3/CD3 and CD4/CD4 Homoconjugates[1]

| Stimulation | Concentration μg/ml | Peak Mean $[Ca^{2+}]i$ (nM) | Increase Above Basal |
|---|---|---|---|
| None | — | 130 | 1.0 |
| CD3/CD4 Heteroconjugate | 10 | 15,600 | 120 |
| | 2 | 10,900 | 83 |
| | 0.4 | 4,140 | 32 |
| | 0.08 | 810 | 6.2 |
| CD3/CD3 Homoconjugate | 50 | 2,360 | 18 |
| | 10 | 559 | 4.3 |
| | 2 | 301 | 2.3 |
| CD4/CD4 Homoconjugate | 100 | 130 | 1.0 |
| | 50 | 130 | 1.0 |
| CD3/CD3 Homoconjugate + CD4/CD4 Homoconjugate | 25 + 25 | 590 | 4.5 |
| | 5 + 5 | 272 | 2.1 |
| | 1 + 1 | 251 | 1.93 |

[1] Assays of $[Ca^{2+}]i$ responses utilized peripheral blood lymphocytes loaded with indo-1 and stained with PE-conjugated anti-CD20, anti-CD8 and anti-CD16 as described above. The unstained cells, comprising >95%, CD4+ cells, were analyzed. The peak mean response occurred within the first five minutes after stimulation.

Effects On Inositol Phosphate Synthesis By The CD3/CD4 Heteroconjugate Of The Invention Because the mobilization of cytoplasmic calcium in T cells is thought to be mediated by the generation of inositol trisphosphate ($InsP_3$), we measured the increase in inositol phosphates after stimulation of purified CD4 T cells with either monoclonal antibody to CD3 alone or with the CD3/CD4 heteroconjugate.

The CD4+T cells were purified as described by June et al., "T-Cell Proliferation Involving The CD28 Pathway Is Associated With Cyclosporine-Resistant Interleukin 2 Gene Expression", *Mol. Cell. Biol.,* 7 (No. 12): 4472–4481 (1987). Briefly, peripheral blood lymphocytes were obtained by leukophoresis of laboratory personnel, followed by Ficoll/Hypaque density gradient centrifugation. The CD4+ subset of T cells were then isolated by negative selection with magnetic bead immunoabsorption after first coating the CD8+, CD11+, CD16+, $CD^{14}$+, and CD20+cells with saturating amounts of the appropriate monoclonal antibody (the majority of antibodies having been referenced earlier, except for the anti-CD14 monoclonal antibody, 20.3, prepared as described by Kamoun et al., "Human Monocyte-Histiocyte Differentiation Antigens Identified By Monoclonal Antibodies", *Clin. Immunoloay and Immunopathology,* 29: 181–195 (1983)). This strategy took advantage of the reciprocal and nonoverlapping distribution of the CD4 and CD8 surface antigens on resting peripheral blood T lymphocytes. The cells were washed three times to remove unbound antibody, and then incubated with goat anti-mouse immunoglobulin-coated magnetic particles (Advanced Magnetics Institute, Cambridge, Mass.) and the bead-coated cells removed by magnetic separation. Typically, approximately 500×10[6] CD4+T cells were recovered that were >98% CD4+ as assessed by flow cytometry and contained <0.1% monocytes as determined by staining for nonspecific esterase.

The purified CD4+ T cells were then resuspended at 2–4×10[6] cells/ml in RPMI 1640 supplemented with 10% heat-inactivated fetal bovine serum ("medium") supplemented with 4 μg/ml PHA and 40 μCi/ml myo-2 [$^3$]-inositol (37 MBq/ml; Amersham Corp., Arlington Heights, Ill.) and incubated at 37° C. in 5% $CO_2$ in air. After 72 h, the cells were washed 3 times and resuspended at 5×10[6] cells/ml in "medium" supplemented with 10 mM LiCl. After a 20 min incubation, G19-4 or the G19-4/G17-2 heteroconjugate was added at T=0 to a final concentration of 1 μg/ml. Then, at various time points, 5×10[5] cells were removed and sedimented for 10 sec in an Eppendorf 5414 centrifuge. After aspiration of the medium, 1 ml of ice cold 10% TCA (w/v) was added to the cellular pellet. After removal of insoluble material by 900×g centrifugation for 5 min, the supernatant was extracted with 6 volumes of diethylether and then neutralized. The [$^3$]-inositol phosphates were separated by anion exchange chromatography using Dowex 1-X8 in formate form (100–200 mesh) (Bio-Rad, Richmond, Calif.) and quantified by liquid scintillation spectroscopy in Bio-Safe 2 (Research Products, Int., Mt. Prospect, Ill.). This procedure for measuring tritiated inositol phosphate has been described by Imboden et al., "Transmembrane Signalling By The T Cell Antigen Receptor", supra and Imboden et al. "Antigen Recognition By A Human T Cell Clone Leads To Increases In Inositol Triphosphate", supra.

Figure 4:
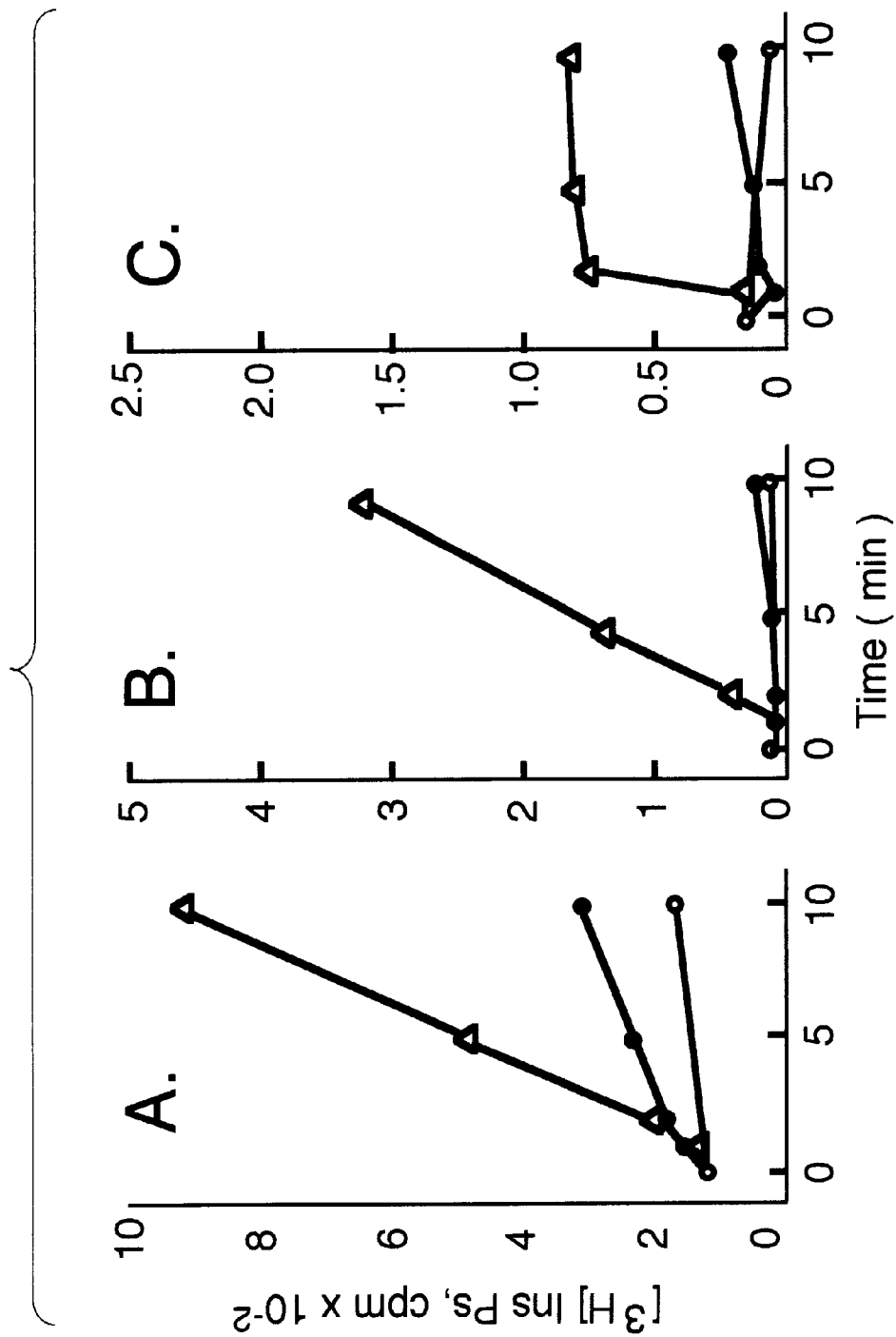
FIG. 4 (A–C) depicts graphical comparative presentations of the increase in inositol phosphates over time upon stimulation of CD4+T cells with anti-CD3, G19-4 (●) or a CD3/CD4 heteroconjugate of the invention, G19-4/G17-2 (Δ) at 1 µg/ml. The inositol phosphate levels in unstimulated controls (o) at t=0 and t=10 min are shown. Panel A depicts the increase in inositol monophosphate ($InsP_1$), panel B depicts the increase in inositol bisphosphate ($InsP_2$) and panel C depicts the increase in inositol trisphosphate ($InsP_3$).

As FIG. 4 demonstrates, at 1 μg/ml, the heteroconjugate stimulated substantial increases in the formation of inositol monophosphate, bisphosphate, and trisphosphate while G19-4 alone caused only a small increase in inositol monophosphate. The tritiated inositol phosphate levels in unstimulated cells at the beginning (t=o) and end of the experiment (t=10 min) are also shown.

Figure 5:
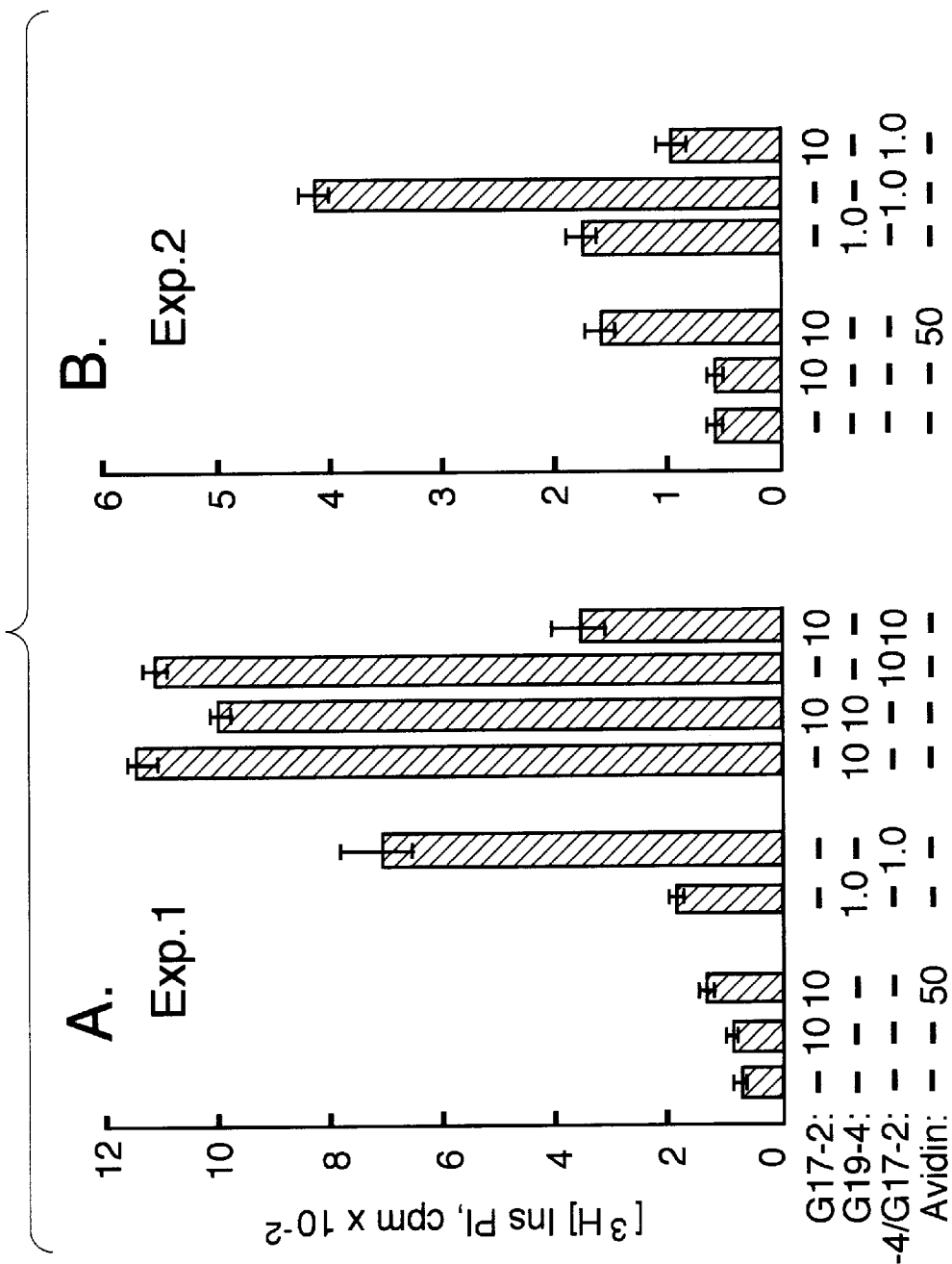
FIG. 5 depicts two independent experiments wherein the increase in $InsP_1$ is measured following the stimulation of $CD^{4+}$ T cells, pretreated with biotin-conjugated anti-CD4 (G17-2), with either anti-CD3 (G19-4), G17-2, a CD3/CD4 heteroconjugate (G19-4/G17-2) or avidin and combinations thereof as indicated.

In additional experiments, depicted in FIG. 5, free monoclonal antibody to CD4, (G17-2), inhibited the inositol phosphate response caused by the heteroconjugate. G17-2 did not inhibit the inositol phosphate response to free anti-CD3 monoclonal antibody, G19-4. According to these experiments, CD4+ T cells were incubated for 72 h in medium containing [$^3$H]-inositol (40 μCi/ml) and PHA (4 μg/ml), washed extensively, and then resuspended in medium with 10 mM LiCl for a 20 min incubation at 37° C. G17-2 (biotin-conjugated as described in Goding, In Monoclonal Antibodies Principles And Practices, p. 230, Academic Press (1983)) was then added to selected samples. After 5 min, G19-4, G17-2, the G19-4/G17-2 heteroconjugate, and avidin were added as indicated, and the incubations were continued for an additional 10 min. Following lysis of the cellular samples ($10^7$ cells/sample) in 10% TCA, [$^3$H]-inositol phosphates were extracted, resolved on anion exchange chromatography, and quantified as described above. Two independent experiments are depicted in FIG. 5. The mean +/– S.E.M. (standard error) for triplicate cellular samples is shown and the final concentration in µg/ml of monoclonal antibody and avidin is given in the figure.

Thus, the experimental data demonstrate not only the enhanced effect of the heteroconjugate of the invention on inositol phosphate production but also that soluble antibody to CD4 inhibits this T cell response. The data suggest therefore the important role the CD4 antigen plays in stimulating T cell responses.

The CD3/CD4 Heteroconjugate Has A Novel Activity In T Cell Activation

It has been discovered that the CD3/CD4 heteroconjugate of the invention possesses a novel functional activity in T cell activation as demonstrated in proliferation assays using CD3/CD3 and CD4/CD4 homoconjugates as controls. In those assays, CD4$^+$ T cells were cultured in quadruplicate samples in flat-bottom, 96 well microtiter plates at $5 \times 10^4$ cells per well in RPMI 1640 medium containing 5% heat-inactivated fetal calf serum (Hyclone, Logan, Utah). The CD4$^+$ cells were cultured for 3 days with either G19-4 (anti-CD3), G19-4/G19-4 (CD3/CD3 homoconjugate), G19-4/G17-2 (CD3/CD4 heteroconjugate) or G17-2/G17-2 (CD4/CD4 homoconjugate) with or without PMA (phorbol myristate acetate) (1 ng/ml) or monoclonal antibody 9.3, an antibody reactive with the CD28 antigen on the T cell surface [(Balb/cxC57BL/6)FI, IgG2a] [see, e.g., Hansen et al., "Monoclonal Antibodies Identifying A Novel T Cell Antigen And Ia Antigens Of Human Lymphocytes", *Immunogenetics* 10: 247–52 (1980)]. All antibodies and conjugates were used at 1 µg/ml. Thymidine incorporation (mean cpm±sem) was determined on day 3 in a liquid scintillation counter after pulsing the cells for the last 8 hours of the 3 day cultures with 1 µci/wall [$^3$H]-thymidine (New England Nuclear Corp., Boston, Mass.).

Figure 6:
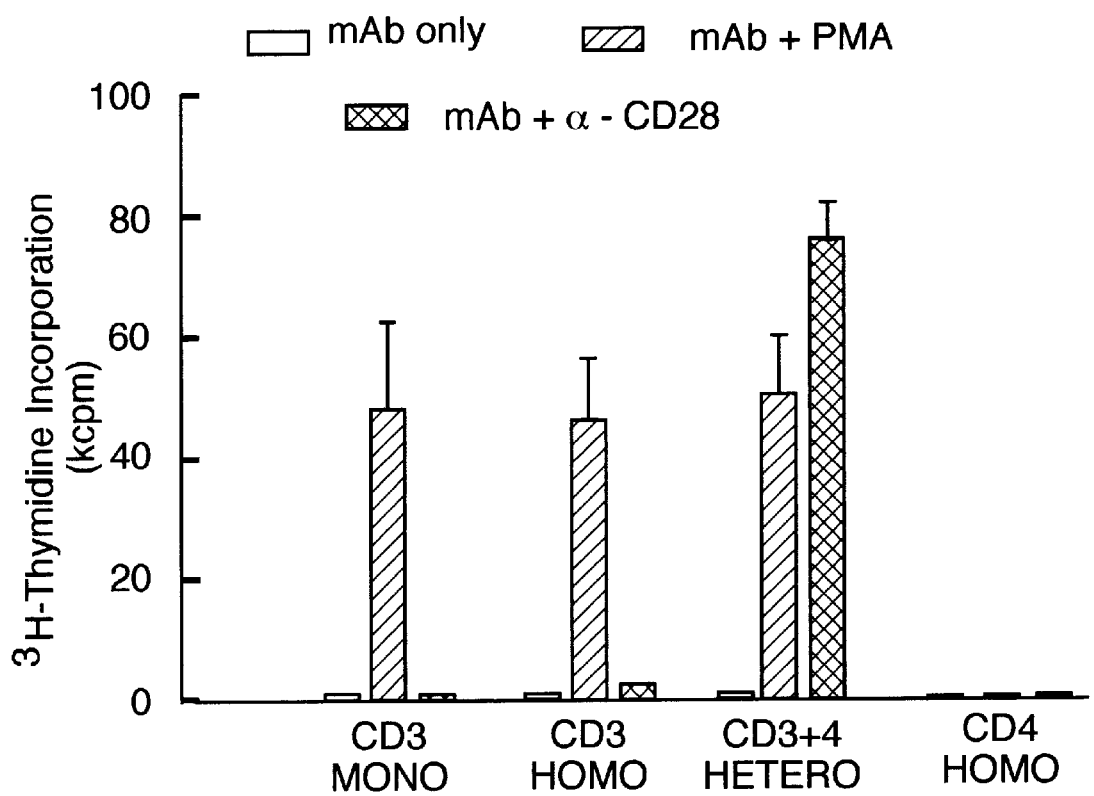
FIG. 6 depicts the effects of an anti-CD3 monoclonal antibody (CD3 Mono), a CD3/CD3 homoconjugate (CD3 Homo), a CD4/CD4 homoconjugate (CD4 Homo) and a CD3/CD4 heteroconjugate of the invention (CD3+4 Hetero) on T cell proliferation as indicated by [3H]-thymidine incorporation by $CD^4+$ T cells, with or without PMA (phorbol myristate acetate) or antibody to CD28.

As shown in FIG. 6, when the purified CD4$^+$ T cells were cultured either with the anti-CD3 reagents alone or with PMA alone, no proliferation was observed. In the presence of PMA, all antibody preparations containing monoclonal antibody to CD3 induced comparable levels of [$^3$H]-thymidine incorporation, whereas the CD4 homoconjugate was not mitogenic. When the various reagents were tested for synergy with the monoclonal antibody to CD28, 9.3, however, substantial differences were observed. Only the CD3/CD4 heteroconjugate induced responsiveness to the CD28 antibody. The CD28 mAb stabilizes induced cytokine mRNAs which are required to induce proliferation [Lindsten et al., *Science* 244:339–343 (1989)]. Previous studies have shown that CD28 stimulation is not mitogenic for purified T cells although monoclonal antibody to CD28 causes >95% of T cells to progress through the cell cycle in the presence of PMA [see, e.g., June et al., *Mol. Cell. Biol.*, supra]. The present finding that CD28 stimulation of purified T cells is not comitogenic with fluid phase CD3 antibodies confirms the previous studies [see, e.g., Weiss et al., "Synergy Between The T3/Antigen Receptor Complex And Tp44 In The Activation Of Human T Cells", J. Immunol., 137 (No. 3): 819–825 (1986)].

Figure 7:
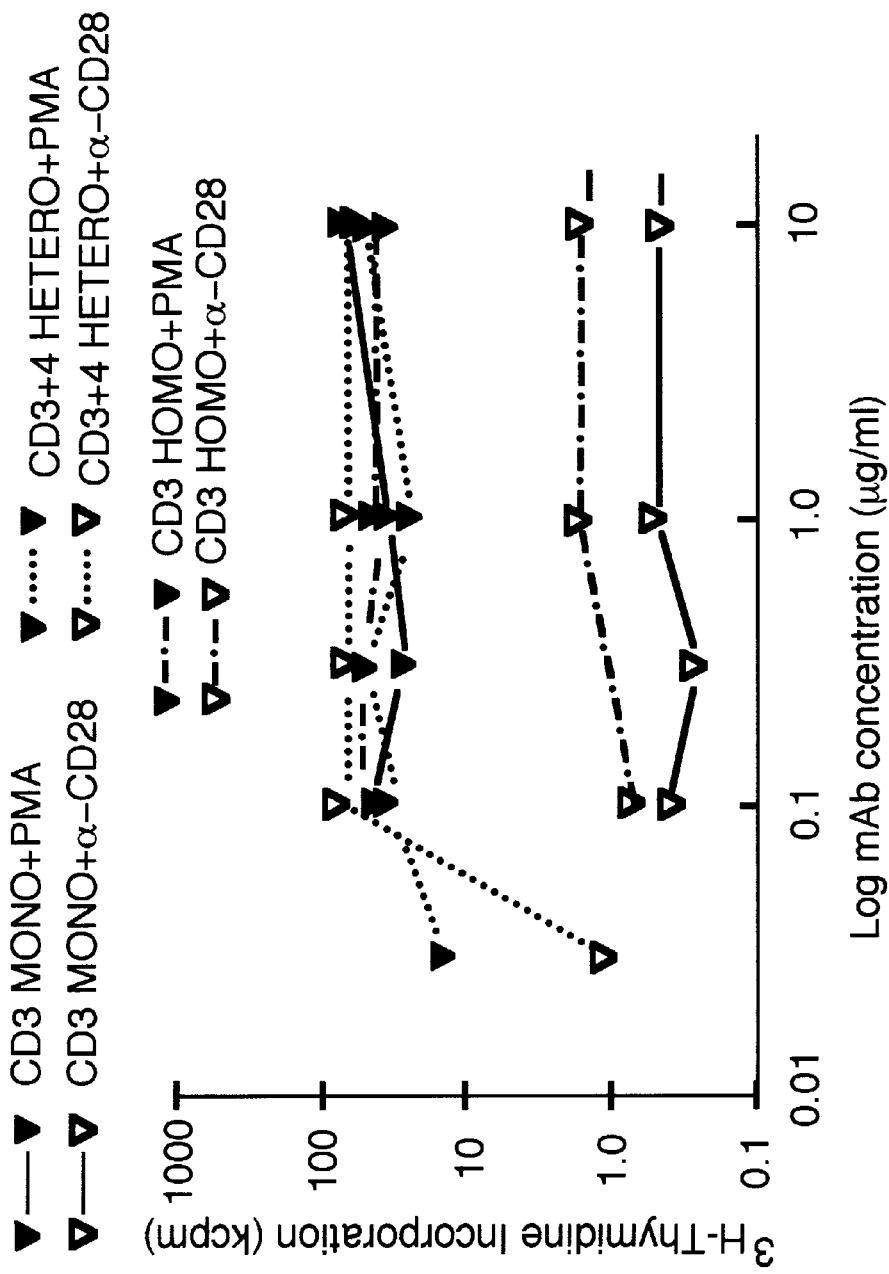
FIG. 7 depicts a comparative graphical presentation of the proliferative response of $CD^4+$ T cells as $^3$H-thymidine incorporation vs. concentration of either G19-4 (CD3 Mono)+PMA (▼-▼), G19-4+anti-CD28 (αCD28) (▽-▽), a CD3/CD4 heteroconjugate (CD3+4 Hetero)+PMA (▼•••▼), a CD3/CD4 heteroconjugate+α-CD28 (▽•••▽), a CD3/CD3 homoconjugate (CD3 Homo)+PMA (▼-•-▼) or a CD3/CD3 homoconjugate +a-CD28 (▽-•-▽).

In order to determine whether the difference between the CD3/CD4 heteroconjugate and the CD3/CD3 homoconjugate with respect to CD28 stimulation was qualitative or quantitative, CD4$^+$ T cells were cultured with G19-4, the G19-4/G17-2 heteroconjugate or the G19-4/G19-4 homoconjugate at various concentrations, with either PMA (1 ng/ml) or anti-CD28 monoclonal antibody, 9.3 (1 µg/ml). As shown in FIG. 7, the G19-4/G17-2 heteroconjugate was found to be fully comitogenic with CD28 stimulation even at concentrations as low as 100 ng/ml whereas the CD3/CD3 homoconjugate was not mitogenic at 10 µg/ml. In contrast, the comitogenic response of cells to PMA and CD3 stimulation was similar for CD3 antibody conjugates at all concentrations tested. Furthermore, kinetic experiments revealed that the difference between the CD3/CD3 homoconjugate and the CD3/CD4 heteroconjugate to CD28 stimulation was not due to a shift in the time course of the proliferation (data not shown).

Thus, it appears that CD4$^+$ T cells that do not respond, by proliferation, to soluble antibody reactive with CD3, do respond to the CD3/CD4 heteroconjugate of the invention by proliferating in the presence of antibody to CD28.

To further examine the effects of the CD3/CD4 heteroconjugate on T cell proliferation, cell cycle kinetics were examined by a technique that allows discrimination of cells in each phase of three sequential cell cycles after stimulation. CD4$^+$ T cells were sorted by flow cytometry on a Cytofluorograph 50 HH cell sorter (Ortho Diagnostic Systems, Inc., Westwood, Mass.) after staining of the cells with PE-conjugated CD8, CD16, and CD20 antibodies (referenced earlier). Negative cells were sorted and these were 97% CD4 positive by reanalysis of the sorted population. In addition to the immunofluorescence parameter, forward scatter and right angle scatter were measured and used to gate on the lymphocyte population and exclude monocytes, debris and dead cells. The cells were sorted with a flow rate of 2000 cells/sec at 20° C.

Sorted cells were cultured in quadruplicate in round bottom, 96 well microtiter plates (Nunc, Kampstrip, Denmark) at $5 \times 10^4$ cells/well. The G19-4/G17-2 heteroconjugate or CD3 or CD4 homoconjugates were added to the cultures at 5 µg/ml or PHA was added at 10 µg/ml. The cells were grown in RPMI 1640 supplemented with 10% FBS in the presence of 0.6 µg/ml anti-CD28 monoclonal antibody, 9.3, $1.5 \times 10^{-4}$ M BrdU, 100 U/ml penicillin and 100 µg/ml streptomycin, and $5 \times 10^{-5}$ M 2-mercaptoethanol. Three days after incubation at 37° C. (5% $CO_2$), the medium was gently aspirated from the wells and replaced with 0.2 ml staining solution containing 0.1 M Tris, pH 7.4, 0.9% NaCl, 1 mM $CaCl_2$, 1.0 mM $MgCl_2$, 0.2% BSA, 0.1% NP40 and 1 ug/ml Hoechst 33258 (Sigma) and 5 ug/ml ethidium bromide, EB (Calbiochem). The cells were incubated for 30 min at 40° C., resuspended, and flow cytometry was performed on an ICP-22 (Ortho Diagnostic Systems, Inc.) interfaced to a PDP11/03 computer (Digital Equipment, Maynard, Mass.), as previously described by Rabinovitch, "Detection Of An Unusually Stable Fibrinolytic Inhibitor Produced By Bovine Endothelial Cells", *Proc. Natl. Acad. Sci. (USA)*, 80: 2956–60 (1983). Ultraviolet excitation (UG1 filter) was used, with Hoechst 33258 emission detected at 425 to 500 nm and fluorescence detected above 600 nm. The fluorescence of approximately $3-4 \times 10^3$ cells was analyzed and recorded as a bivariate histogram of Hoechst versus EB fluorescence. Determination of individual cell cycle compartment sizes was by analysis and curve fitting as previously reported by Rabinovitch, id.

Figure 8:
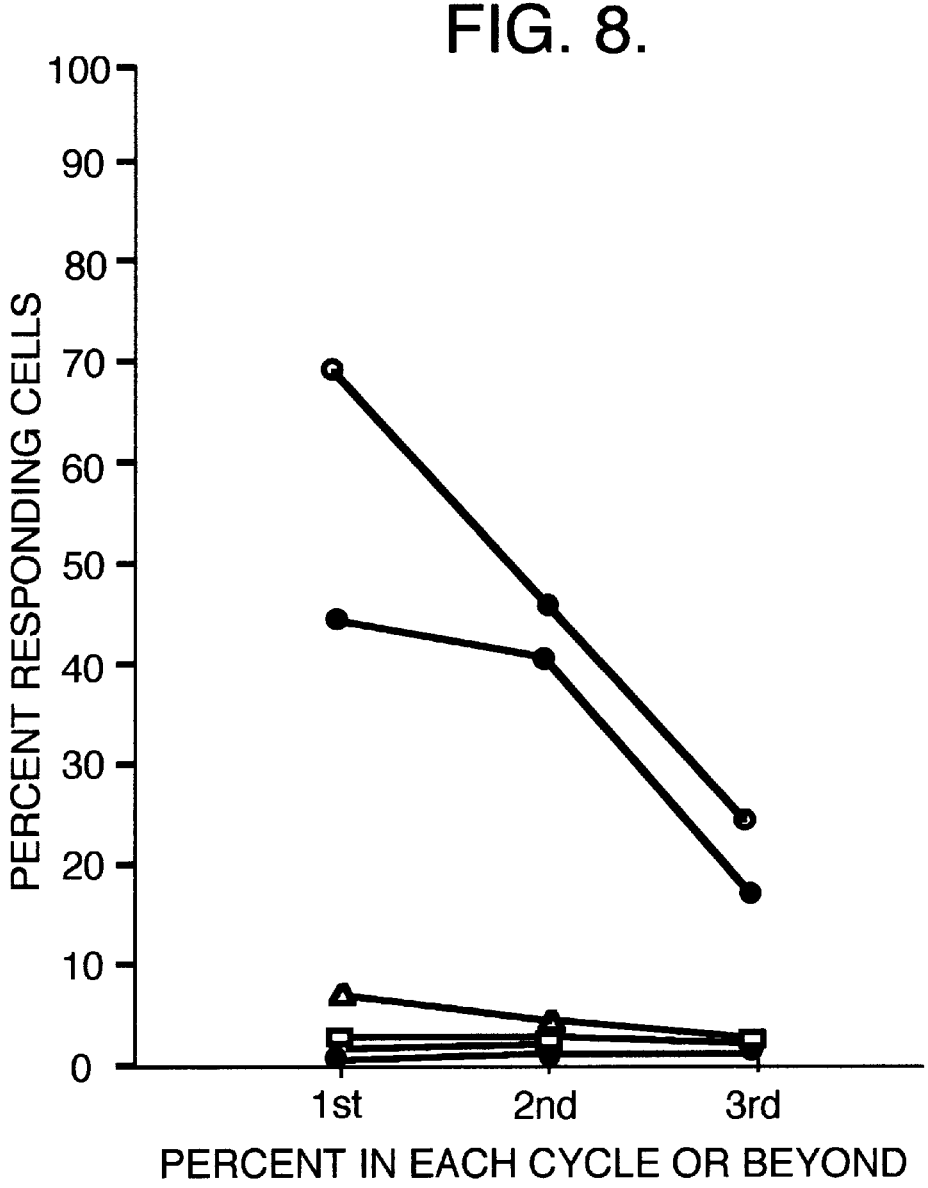
FIG. 8 depicts the percentage of CD4+ T cells past the first, second or third cell cycles after stimulation of the T cells for 3 days with either PHA (phytohemag-glutinin), a CD3/CD4 heteroconjugate of the invention, G19-4/G17-2, a CD3/CD3 homoconjugate, G19-4/G19-4, a CD3/CD8 heteroconjugate as control, G19-4/G10-1, and a CD4/CD4 homoconjugate, G17-2/G17-2.

The percentage of cells past the first, second or third cell cycles are shown in FIG. 8. As the figure demonstrates, only the CD3/CD4 heteroconjugate was able to significantly drive the cells through the cell cycle, as 45% of cells entered S phase or beyond and 39% of cells entered a second cycle of proliferation after 3 days of stimulation with the heteroconjugate. Thus, the [³H]-thymidine incorporation by purified CD4⁺ cells in response to the CD3/CD4 heteroconjugate plus anti-CD28 stimulation (as shown in FIGS. 6 and 7) represents a substantial proliferative response that persisted into a second and third generation. In contrast, none of the other antibody preparations could induce significant cell cycle transition (see FIG. 8).

FIG. 8 also indicates that, in comparison to the PHA plus anti-CD28 control, where 70% of the sorted cells had entered S phase after three days of culture, 45% of cells stimulated by the CD3/CD4 heteroconjugate had responded. This indicates that a significant number of CD4⁺ cells had cell cycle progression after stimulation with the CD3/CD4 heteroconjugate.

The CD3/CD4 Heteroconiugate Comodulates The CD3 And CD4 T Cell Antigens

The modulation of CD3 and CD4 antigens on the T cell surface by the CD3/CD4 heteroconjugate, CD3 or CD4 homoconjugates or antibody to CD4 or CD3 alone was measured by determining the density of antibody or antibody conjugates on the surface of CD4⁺ T cells after an 18 h incubation at 37° C. in the presence of 10 μg/ml antibody or antibody conjugate, using immunofluorescence with an anti-mouse Ig second step and measured on a FACS IV flow cytometer. The results are shown in Table II below, wherein density is expressed as units of mean fluorescence intensity over background measured on a linear scale.

TABLE II

Modulation By Conjugates

| Specificity | Surface Density Before Modulation | Surface Density After Modulation | Percent Modulation |
|---|---|---|---|
| CD4 | 150 | 48 | 68 |
| CD4/CD4 Homoconjugate | 226 | 75 | 67 |
| CD3 | 177 | 9 | 95 |
| CD3/CD3 Homoconjugate | 340 | 10 | 99 |
| CD3/CD4 Heteroconjugate | 369 | 19 | 95 |

As the table indicates, overnight incubation with antibody to CD3 or a CD3/CD3 homoconjugate resulted in an almost undetectable surface expression of CD3, whereas significant amounts of surface CD4 still remained after similar incubation with antibody to CD4 or a CD4/CD4 homoconjugate. The CD3/CD4 heteroconjugate however caused the modulation of both CD3 and CD4 and appeared to decrease the surface expression of CD4. All antibodies and conjugates used in these assays were in excess since no cell surface free CD3 or CD4 antigen (i.e., unbound by antibody) was detectable after modulation, when assayed using direct fluorescence conjugates of anti-CD3 or anti-CD4 monoclonal antibodies (data not shown). Thus, the CD3/CD4 heteroconjugate of the invention comodulates the CD3 and CD4 antigens on the surface of T cells, indicating that the heteroconjugate is not simply anchoring the T cell receptor to the cell surface as has been proposed in the case of immobilized antibody to CD3 [see, e.g., Ledbetter et al., *J. Immunol.*, supra]. Furthermore, studies with soluble anti-CD3 have indicated that when CD3 is modulated from the cell surface, the CD3/Ti receptor is internalized [see, e.g., Press et al., "Evaluation Of Ricin A Chain Immunotoxins Directed Against Human T Cells", *Cellular Immunol.,* 102: 10–20 (1986) and Press et al., "Endocytosis And Degradation Of Murine Anti-Human CD3 Monoclonal Antibodies By Normal And Malignant T Lymphocytes", *Cancer Research,* 48:2249–2257 (1988)] leading to inhibition of T cell activation. The heteroconjugates of this invention also lead to the internalization of the receptor, yet T cell activation is enhanced.

As this example demonstrates, the CD3/CD4 heteroconjugate of this invention enhances both $[Ca^{2+}]_i$ mobilization and inositol phosphate production in the activation of CD4⁺ T cells. In addition, the heteroconjugate possesses a novel functional activity in the proliferation of CD4⁺ T cells in the presence of antibody to CD28, driving a significant fraction of the cells into a second cell cycle within the first three days of stimulation. Furthermore, the heteroconjugate appears to comodulate the antigens with which it is reactive, supporting the hypothesis that it acts to bring those antigens into close proximity in the activation of the T cells.

EXAMPLE 2

The following example describes the construction and characterization of other heteroconjugates of the invention, comprised of an antibody reactive with the CD3 antigen cross-linked to any of a number of other antibodies reactive with CD T cell antigens.

The antibody heteroconjugates, constructed as described in Example 1 above, were: a) a CD3/CD2 heteroconjugate comprising monoclonal antibodies G19-4 (anti-CD3) (referenced earlier) and 9.6 (anti-CD2), [see, e.g., Martin et al., "Identification And Functional Characterization Of Two Distinct Epitopes On The Human T Cell Surface Protein Tp50", *J. Immunol.,* 131: 180 (1983)]; b) a CD3/CD5 heteroconjugate comprising monoclonal antibodies G19-4 and 10.2 (anti-CD5) [see, e.g., P. J. Martin et al., "A New Human T-Cell Differention Antigen; Unexpected Expression On ) Chronic Lymphocytic Leukemic Cells", *Immunogenetics.* 11: 429 (1980) and Martin et al., "Monoclonal Antibodies Recognizing Normal Human T Lymphocytes And Malignant B Lymphocytes A Comparative Study", *J. Immunol.,* 12: 1920 (1981)]; c) a CD3/CD6 heteroconjugate comprising monoclonal antibodies G19-4 and G3-6 (anti-CD6) (G3-6 is an anti-CD6 monoclonal antibody of the IgGl isotype produced by immunization of Balb/c mice with the T leukemia cell line, HSB2. Hybridomas were produced by the fusion of spleen cells from the mice with the NS1 myeloma line and screened by binding to normal T cells and cross-blocking with a CB6 reference antibody, 12.1 [see, e.g., Martin et al., *J. Immunol.,* 127, supra; d) a CD3/CD7 heteroconjugate comprising monoclonal antibodies G19-4 and G3-7 (anti-CD7) (G3-7 is an anti-CD7 monoclonal antibody of the IgGl isotype produced by immunization of Balb/c mice with the T leukemia cell line, HSB2. Hybridomas were produced by the fusion of spleen cells from the mice with the NS1 myeloma line and screened by binding to normal T cells and cross-blocking with a CD7 reference antibody, 3A1, available from the American Type Culture Collection. In addition, an anti-CD7 monoclonal antibody is commercially available (Becton Dickinson, Mountainview, Calif.)) [see also, e.g., Reinherz et al. (eds.), *Leukocyte Typing II,* Vol. 1, pp. 3–30 (1986)]; 20 e) a CD3/CD8 heteroconjugate comprising monoclonal antibodies G19-4 and G10-1 (anti-CD8) (referenced earlier); and f) a CD3/CD28 heteroconjugate comprising monoclonal antibodies G19-4 and 9.3 (referenced earlier).

These heteroconjugates were tested for their ability to enhance the mobilization of cytoplasmic $Ca^{2+}$ in T cells as described in Example 1. Each heteroconjugate was tested at 1 μg/ml, a concentration at which the activity of antibody to CD3 alone is suboptimal and enhanced activity of the conjugates is detected. Peak $[Ca^{2+}]_i$ responses of indo-1 loaded peripheral blood lymphocytes occurred within the first 5 min. after stimulation of the cells with the heteroconjugate. Unstimulated cells showed a $[Ca^{2+}]_i$ of 130 nM. In the experiments with the CD3/CD4 and CD3/CD8 heteroconjugates, the activity of the conjugate was measured on CD4+ and CD8+ T cell subsets, respectively. The activity of these heteroconjugates in calcium mobilization is shown in Table III below.

TABLE III

Activity of Anti-CD3 Heteroconjugates in Calcium Mobilization

| Conjugate | Peak $[Ca^{2+}]_i$ (nM) |
|---|---|
| CD3/CD3 (G19-4/G19-4) | 186 |
| CD3/CD2 (G19-4/9.6) | 2722 |
| CD3/CD4 (G19-4/G17-2) | 3349 |
| CD3/CD5 (G19-4/10.2) | 155 |
| CD3/CD6 (G19-4/G3-6) | 836 |
| CD3/CD7 (G19-4/G3-7) | 276 |
| CD3/CD8 (G19-4/G10-1) | 2690 |
| CD3/CD28 (G19-4/9.3) | 204 |

As Table III indicates, the CD3/CD2, CD3/CD6, CD3/CD7 and CD3/CD8 heteroconjugates (as well as the CD3/CD4 heteroconjugate) caused a marked increase in calcium mobilization within the T cells treated with those heteroconjugates as compared to the activity of unstimulated or CD3/CD3-stimulated cells. It is believed that these heteroconjugates, like the CD3/CD4 heteroconjugate described in Example 1, act by bringing the respective antigens they react with into close proximity, resulting in enhanced transmembrane signalling and T cell activation.

EXAMPLE 3

This example describes the construction and characterization of still other heteroconjugates of the invention, comprised of an antibody reactive with the CD5 T cell surface antigen cross-linked to any of a number of other CD T cell antigens.

These antibody heteroconjugates, constructed as described above in Example 1, were the following: a) a CD5/CD2 heteroconjugate comprising monoclonal antibodies 10.2 and 9.6; b) a CD5/CD28 heteroconjugate comprising monoclonal antibodies 10.2 and 9.3; c) a CD5/CD4 heteroconjugate comprising monoclonal antibodies 10.2 and G17-2; d) a CD5/CD6 heteroconjugate comprising monoclonal antibodies 10.2 and G3-6; e) a CD5/CD7 heteroconjugate comprising monoclonal antibodies 10.2 and G3-7; and f) a CD5/CD8 heteroconjugate comprising monoclonal antibodies 10.2 and G10-1. All the monoclonal antibodies utilized to construct the heteroconjugates of this embodiment have been referenced earlier.

These heteroconjugates were also tested for their ability to enhance the mobilization of cytoplasmic $Ca^{2+}$ in T cells as described in Example 1. The results of these experiments are shown in Table IV below. The concentration of each heteroconjugate used in these experiments is indicated in the table. Peak $[Ca^{2+}]_i$ responses of the indo-1 loaded peripheral blood lymphocytes occurred within the first 10 min after stimulation. Unstimulated cells showed a $[Ca^{2+}]_i$ of 130 nM. As the table shows, a CD5/CD5 homoconjugate displayed a $[Ca^{2+}]_i$ of 180 nM. The CD5/CD4 and CD5/CD8 heteroconjugates were tested on CD4+ and CD8+ T cell subsets, respectively.

TABLE IV

Activity of Anti-CD5 Heteroconjugates in Calcium Mobilization

| Conjugate | Peak $[Ca^{2+}]_i$ (nM) |
|---|---|
| CD5/CD5 (10.2/10.2, 20 µg/ml) | 180 |
| CD5/CD2 (10.2/9.6, 20 µg/ml) | 204 |
| CD5/CD28 (10.2/9.3, 10 µg/ml) | 196 |
| CD5/CD4 (10.2/G17-2, 2 µg/ml) | 640 |
| CD5/CD6 (10.2/G3-6, 2 µg/ml) | 421 |
| CD5/CD7 (10.2/G3-7, 15 µg/ml) | 178 |
| CD5/CD8 (10.2/G10-1, 2 µg/ml) | 546 |

As Table IV indicates, the CD5/CD4, CD5/CD6 and CD5/CD8 heteroconjugates show a significant increase in calcium mobilization compared with unstimulated or CD5/CD5-stimulated cells. It is believed that these heteroconjugates, like the other heteroconjugates described herein, are useful in the enhanced activation of T cells.

EXAMPLE 4

In this example a heteroconjugate consisting of antibodies reactive with CD3 and CD45 antigens was used to investigate the effect of interactions between the CD3 and ) CD45 surface antigens on the activation of T cells.

Cell Preparations. Peripheral blood mononuclear cells, and nylon wool nonadherent lymphocytes from peripheral blood were prepared as previously described [(Clark et al., *Proc. Natl. Acad. Sci. (USA)* 82:1766–1770 (1985) and Clark et al., *Hum. Immunol.* 16: 100–113 (1986), both incorporated by reference herein]. Briefly, nylon wool nonadherent lymphocytes were obtained by nylon wool separation as follows: a nylon column (prepared at Oncogen, Seattle, Wash.) was loaded with RPMI medium containing 5% fetal calf serum and was used after pre-incubation for 45 min. at 37° C. Cells were applied to the column and allowed to flow into the column and then incubated at 37° C. for 45 min. Using warm media 6 mls were collected off the column, spun twice for 8 min at 1200 rpm then resuspended in proliferation buffer (15% human AB sera) (approximately 1.5 ml). The nonadherent cells were counted and the volume adjusted accordingly for use in the assays.

The following Balb/c mouse mAbs to human leukocyte markers were used: 9.4 (IgG2a), anti-CD45 [Cobbold, supra]; G1-15 (IgG1) and 3AC5 (IgG2a), anti-CD45R [Ledbetter, supra and Ledbetter, et al., *In Perspectives in Immunogenetics and Histocompatibility*, ed. Heise,. (ASHI, New York) pp. 325–340]; 96.5 (Brown et al., *J. Immunol.* 127(2):639–546 (1981)). UCHL-1 (IgG1) antibodies (180 form) kindly provided by Dr. P. Beverley [Smith, supra]; G19-4 (IgG1), anti-CD3 [Ledbetter, supra]; 9.6 anti-CD2, (referenced earlier); and 9.3, anti-CD28 (referenced earlier). The rat anti-mouse kappa (k)-specific, mAb, 187. 1 [Yelton et al., *Hybridoma* 1:5 (1981)] was used to cross-link mouse mAb.

Preparation of mAb Heteroconiugate. The monoclonal antibody heteroconjugates were prepared at a 1:1 molar ratio with the heterobifunctional cross-linker GMBS (Calbiochem, La Jolla, Calif.) and 5-iminothiolane HCl (Pierce Chemical Co., Rockford, Ill.) as described above in Example 1. More particularly, antibodies (1 mg/ml) were dialyzed overnight against coupling buffer (0.1 M Na₂HPO₄-dibasic, seven-hydrate 0.1 M NaCl, pH 7.5). The first antibody of the conjugate was thiolated with iminothiolane-HCl salt (2-IT from Pierce Chemical Co., Rockford, Ill.) by adding 50 μl (0.5 mg) of 2-IT solution (10 mg/ml in coupling buffer) while mixing. The second antibody of the conjugate was treated with 5 μl GMBS (14 ug of GMBS solution (1 mg in 360 μl dimethylformamide (DMF)). The solutions were incubated for 1 hr at room temperature. The antibodies were run over separate PD-10 columns (Pharmacia, Uppsala, Sweden) pre-equilibrated in coupling buffer. After a void volume of 2.6 ml total, antibody was collected in double the original volume. The antibodies were mixed and incubated at room temperature for 5 hrs, and reactions were quenched by the addition of 1 μl of 25 mM B-mercaptoethanol (1 μl:560 μl coupling buffer) and a 15 min. incubation at room temperature. This reaction was stopped by addition of 11 μl (11 μg) of N-ethylmaleimide (Sigma Chemical Co., St. Louis, Mo.) made up to 1 mg/ml in DMF.

Conjugates were dialyzed overnight against phosphate buffered saline (PBS). The resulting CD3/CD45 heteroconjugate was separated from free antibodies on Superose 6 FPLC as described in Example 1, and designated G19-4/9.4.

Conjugation of mAbs with biotin utilized biotinsuccinimide (Sigma Chemical Co., St. Louis, Mo.) as previously described [Hardy, (1986) In Handbook of Experimental Immunology, (ed., Weir et al.), (Blackwell, Oxford) pp. 31.1–31.2 (1986)), incorporated by reference herein. Phorbol-12-myristate-13-acetate (PMA) and avidin were from Sigma Chemical Co., St. Louis, Mo. Recombinant interleukin 2 (rIL2) was purchased from Genzyme (Boston, Mass.) and was used to promote proliferation in some assays.

Proliferation of blood T Cells was measured by incorporation of [$^3$H]thymidine (New England Nuclear; specific activity 27 Ci/mmol; 1 Ci=37 GBq) as described above in Example 1 using $10^6$ cells per ml in 200 μl microtiter wells. More particularly, for the proliferation assays, mononuclear cells were cultured as described by Ledbetter et al., in Journal Immunol. 135:1819–1825 (1985), incorporated by reference herein. Briefly, mononuclear cells were isolated from peripheral blood by density centrifugation on Ficoll-Hypaque followed by adherence to plastic to remove the majority of monocytes. Cells were cultured at $2.5 \times 10^5$/ml in quadruplicate samples in 96-well microtiter plates (Falcon, Becton-Dickenson, Oxnard, Calif.) in RPMI medium containing penicillin, streptomycin, and 15% human AB serum (Pel Freez, Brown Deer, Wis.). Either the mitogen phytohemagglutinin (PHA; Wellcome Diagnostics, Greenville, NC) or anti-CD3 mAb (G19-4) coupled to Sepharose was used to stimulate T cells. After 3 or 4 days in culture, wells were pulsed for 6 hr with 0.5 μCi [$^3$H]thymidine/well (New England Nuclear, Boston, Mass.; 6.7 CimMol specific activity). Cells were then harvested onto glass fiber filters by using a cell harvester, and radioactivity was measured in a liquid scintillation counter. In some experiments, recombinant IL2 (rIL-2; Genzyme, Boston, Mass.) was used at 25 U/ml. Measurements of [3H]thymidine uptake were taken during the last 6 hr. of a 3-day experiment using mAb G19-4 precoated to the wells of the microtiter plate at 10 μg/ml prior to the assay. The concentration of anti-CD45 mAb 9.4 in solution was 1 μg/μl and was immobilized on the microtiter plate at 10 μg/ml. Cells were cultured in quadruplicate and means are shown. Standard errors were <11%.

TABLE V

Table V summarizes the results.
CD45 regulates T-cell proliferation
After Stimulation of-CD3

| | | Proliferation ([$^3$H])thymidine incorporation, cpm × $10^{-3}$) | | |
|---|---|---|---|---|
| Activation | PMA (1 ng/ml) | Medium | Anti-CD45 in Solution | Anti-CD45 Immobilized |
| Medium | − | 0.3 | 0.4 | 0.3 |
| | + | 0.5 | 0.5 | 0.4 |
| Anti-CD3 | − | 137.9 | 143.5 | 32.3 |
| immobilized + | + | 204.3 | 198.3 | 93.2 |
| rIL-2 100 units/ml | − | 196.3 | 183.9 | 67.1 |

Table V shows that anti-CD45 immobilized together with anti-CD3 inhibited T cell proliferation by more than 75%, whereas anti-CD45 in solution did not. The inhibitory effect of immobilized anti-CD45 was still apparent even in the presence of a suboptimal concentration of PMA or exogenous rIL2.

Proliferation of T cells after stimulation with anti-CD3 mAb (G19.4) was also measured with immobilized anti-CD3 mAb and CD45R mAbs (G1-15 and 3AC5) immobilized or in solution. Proliferation was measured as described above for anti-CD45. Anti-CD45R mAbs G1-15 and 3AC5 were used at 1 μg/ml in solution and immobilized at 10 μg/ml. A control IgG2a mAb 96.5 against melanoma antigen p97 was used as a nonreacting control at 1 μg/ml in solution and 10 μg/ml immobilized. Table VI shows the results of this experiment.

TABLE VI

CD5 regulates T-cell proliferation
After Stimulation of CD3

| | Proliferation ([$^3$H]thymidine incorporation, cpm × $10^{-3}$) | | |
|---|---|---|---|
| Activation | Medium | PMA (1 ng/ml) | rIL-2 100 units/ml |
| Medium | 0.1 | 0.5 | 0.4 |
| Anti-CD3 immobilized | | | |
| + medium | 143.6 | 281.5 | 291.8 |
| + G1-15 anti-CD45R (soln) | 137.5 | 261.5 | 309.4 |
| + 3AC5 anti-CD45R (soln) | 177.8 | 266.2 | 294.6 |
| + 96.5 (soln) | 147.9 | 262.1 | 312.4 |
| Anti-CD3 immobilized | | | |
| + G1-15 anti-CD45R (immobiiized) | 0.1 | 0.7 | 0.6 |
| + 3ACS anti-CD45R (immobilized) | 10.1 | 68.2 | 95.5 |
| + 96.5 immobilized | 154.4 | 247.1 | 280.4 |

Inhibition was evident when either CD45R (3AC5) or CD45R (G1-15) mAbs were immobilized together with anti-CD3, but not when the CD45R mAbs were in solution. Again, neither PMA nor rIL2 could overcome this inhibition. The control mAb, 96.5, against the melanoma antigen p97, did not inhibit proliferation in response to immobilized anti-CD3 when either present in solution or immobilized together with anti-CD3.

Figure 9:
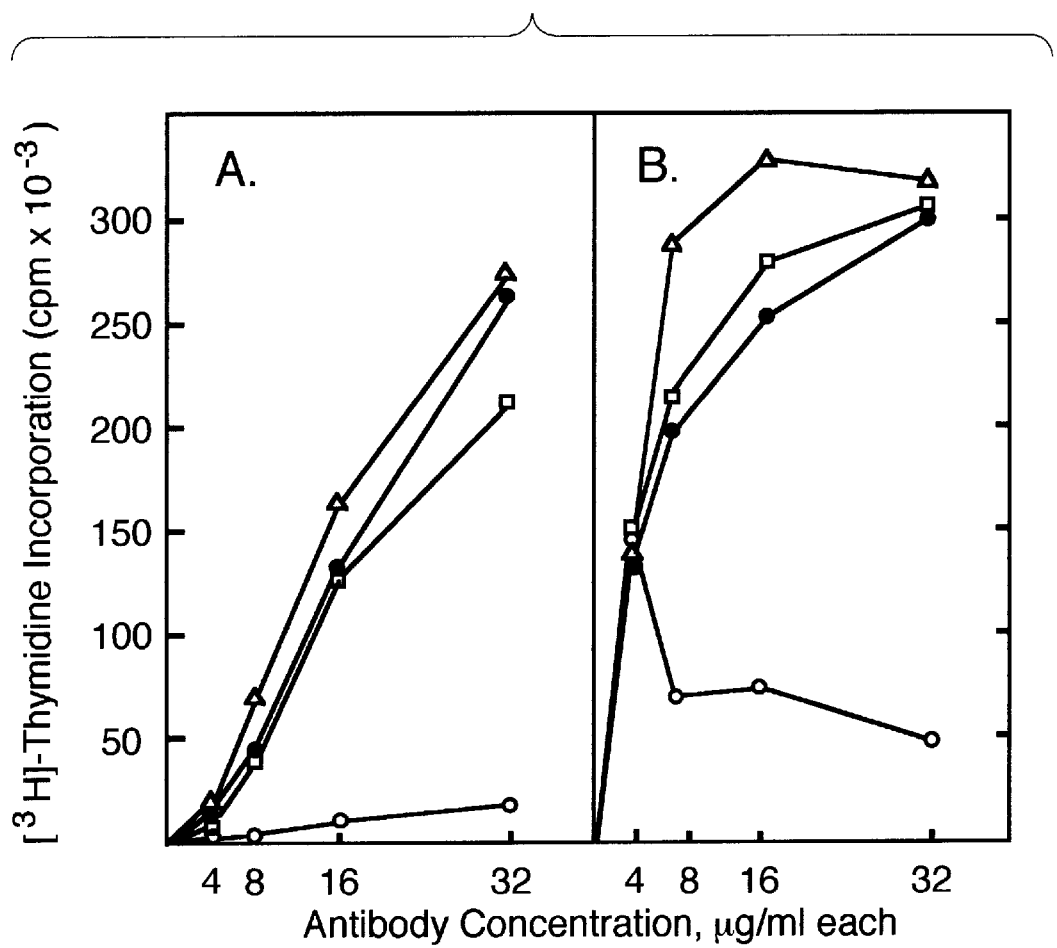
FIG. 9 (A–B) depicts a comparative graphical presentation of inhibition of the proliferative response of T cells induced by immobilized anti-CD3 mAb G19-4 as indicated by [$^3$H]-thymidine incorporation either alone (●) or vs. concentration of either anti-CD45 mAb 9.4 (o) or anti-p97 mAb 96.5 (☐), without (A) or with (B) PMA, (proliferation with anti-CD45 mAb 9.4 in solution (Δ) is also shown for comparison; means are shown; standard errors were <15%).

To ensure that the inhibition seen with immobilized CD45 mAb (9.4) was not due simply to a displacement of the CD3 mAb (G19-4) from the plastic surface, microtiter wells were coated with anti-CD3 alone, anti-CD3 plus anti-CD45, or anti-CD3 plus the control mAb 96.5. Peripheral blood mononuclear cells were stimulated with anti-CD3 mAb G19-4 immobilized to the walls of a microtiter plate by incubation at room temperature in phosphate buffered saline for 2 hr. at concentrations of 4, 8, 16 and 32 µg/ml, either alone or together with anti-CD45 mAb 9.4 or with a control mAb 96.5 at the same concentration as the anti-CD3 mAb. Bovine serum albumin was added to permit further protein attachment. Proliferation with CD45 mAb 9.4 in solution was used for comparison. Proliferation was measured in the absence or presence of PMA at 1 ng/ml. Cells were cultured in quadruplicate for 3 days and pulsed with [$^3$H]thymidine during the last 6 hr. FIG. 9 presents the results of these experiments (means are shown and standard errors were less than 15% of the mean at each point).

FIG. 9 shows that (a) as more anti-CD3 was used for coating the wells, there was more proliferation, consistent with previous reports (Geppert et al., *J. Immunol.* 138: 1660–1666 (1987)); (b) the CD45 mAb 9.4 caused substantial inhibition at all concentrations only when immobilized; and (c) there was essentially no inhibition caused by the simultaneous coating with the isotype control 96.5 mAb, indicating that the inhibition by anti-CD45 was not the result of a displacement of anti-CD3. Addition of 1 ng/ml PMA to the cultures reversed the inhibition by immobilized anti-CD45 only when the mAb was coated at 4 µg/ml or less, but not in higher concentrations (FIG. 9B). This suggests that a critical concentration of anti-CD45 may need to be in close proximity to anti-CD3 on the plastic surface to maintain inhibition in the presence of PMA.

T cell activation resulting in proliferation can proceed by stimulation of CD28 and CD2 using mAbs 9.3 and 9.6 in solution, respectively, with subsequent cross-linking in a second step using anti-k mAb 187.1 8 Van Lier et al., *Eur. J. Immunol.* 18:167–175 (1988) and Ledbetter et al., *Proc. Natl. Acad. Sci. USA* 84:1384–1388 (1987)]. To investigate the effects of CD45 ligation in this system, anti-CD45 was added to anti-CD28 or to anti-CD2 in solution with or without the cross-linking mAb 187.1. [Yelton et al., supra]. Proliferation was measured by [3H]thymidine uptake as described above. Anti-CD28 mAb 9.3 and anti-CD2 mAb 9.6 were used for activation at 1 µg/ml each. Anti-CD45 mAb 9.4 was used at 1 µg/ml and anti-k mAb 187.1 was used to cross-link the antibodies at a 4:1 final ratio of mAb 187.1 to mouse mAb. Proliferation was measured in the presence (100 Units/ml) and absence of rIL-2. Table VII shows the results (standard errors were <12% of the mean at each point).

TABLE VII

CD45 regulates T-cell proliferation
After CD2 and CD28 Simulation

| Stimulus | (100 units/ml) | Proliferation ([$^3$H]thymidine incorporation, cpm × 10$^{-3}$) | | |
|---|---|---|---|---|
| | | Medium | mAb 187.1 | Anti-CD45 | Anti-CD45 + mAb187.1 |
| Medium | − | 0.2 | 0.3 | 1.6 | 0.4 |
| | + | 6.8 | 4.2 | 37.6 | 2.5 |
| Anti-CD28 | − | 0.2 | 4.3 | 47.4 | 0.4 |
| | + | 12.6 | 36.1 | 72.5 | 9.6 |
| Anti-CD2 | − | 0.5 | 0.2 | 12.7 | 0.2 |
| | + | 4.4 | 7.0 | 37.3 | 4.0 |

It is apparent that addition of anti-CD45 alone could promote cell proliferation or increase that induced by either CD2 or CD28 mAbs without requiring exogenous rIL2 (Table VII). In all instances, addition of rIL2 further augmented cell proliferation even in the absence of other stimulants. These phenomena may be due to an effect of CD45 ligation on expression of high affinity receptors for IL2 (Ledbetter, supra).

In contrast, cross-linking CD45 to CD2 or CD28 by addition of the 187.1 anti-K mAb reversed the stimulatory effect of CD45 alone and reduced the stimulation by CD2 or CD28 (Table VII) in either the presence or absence of rIL2. This was not due to a nonspecific inhibitory activity of 187.1 since CD28 or CD2 stimulation were both enhanced by 187.1 when the CD45 mAb 9.4 was not included.

Figure 10:
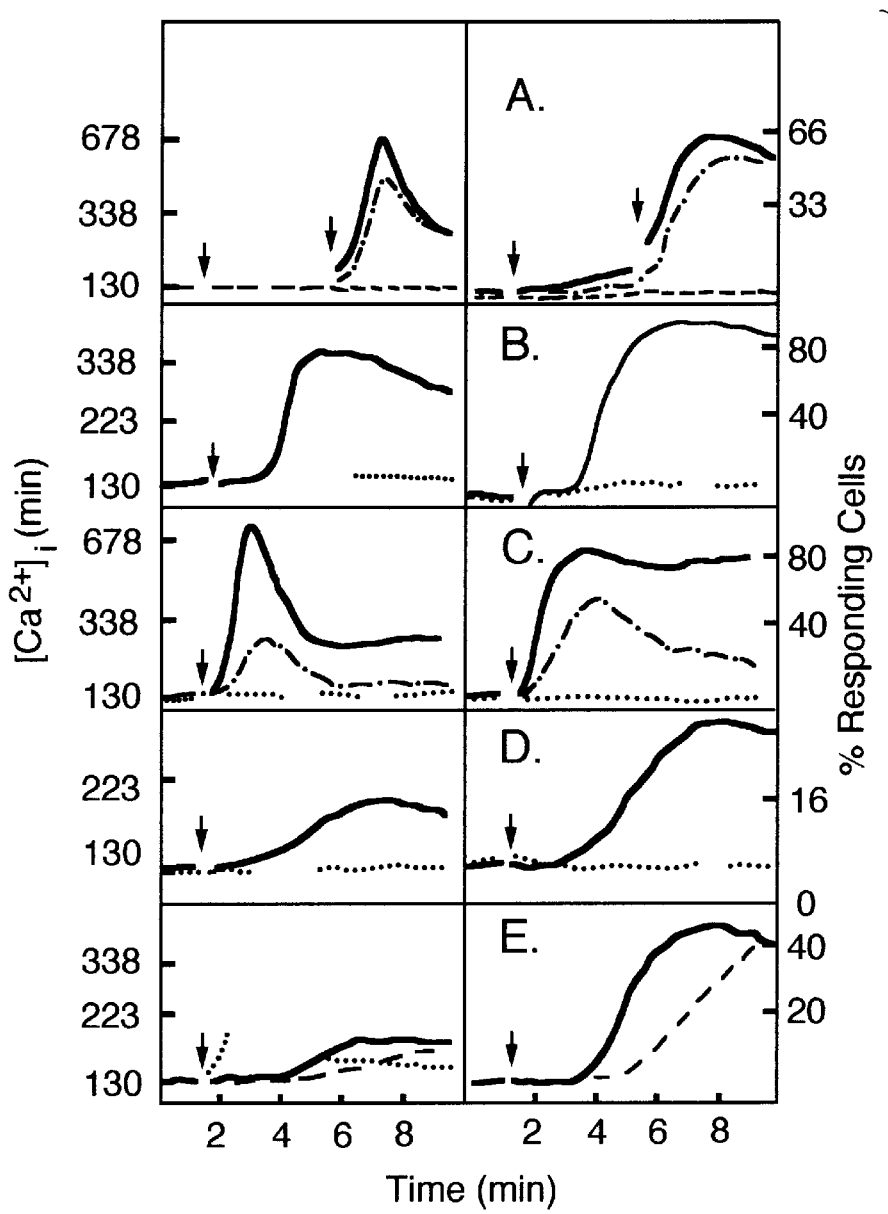
FIG. 10 are graphs depicting the regulation of signal transduction in T cells by the CD45 receptor as determined by increases in $[Ca^{2+}]_i$ over time after cross-linking receptors on T cells either alone or together with anti-CD45 mAb 9.4 or anti-CD45R mAb 3AC5 as described in Example 4, infra. (Mean $[Ca^{2+}]_i$ is shown on the left, and percentage of responding cells is shown on the right for each experiment; arrows indicate time of addition of mAbs or avidin).

CD3, CD2, and CD28 are coupled to signal transduction pathways that result in an increase in $[Ca^{2+}]_i$ when these receptors are ligated on the cell surface. [Ledbetter et al., *Proc. Natl. Acad. Sci. USA* 84:1384–1388 (1987)]. $[Ca^{2+}]_i$ was measured after cross-linking the CD3, CD2 or CD28 receptors in the presence or absence of CD45 mAb 9.4 (FIG. 10). In this experiment, biotin-conjugated mAbs were bound to peripheral blood T cells and then crosslinked on the cell surface by the addition of avidin. Increases in $[Ca^{2+}]_i$ in peripheral blood mononuclear T cells loaded with indo-1 (Molecular Probes, Junction City, Oreg.) were measured after cross-linking receptors on T cells either along or together with anti-CD45 mAb 9.4 or anti-CD45R mAb 3AC5 as follows (conditions are set forth with reference to FIG. 10):

1. The CD3 receptor was cross-linked with biotin-conjugated anti-CD3 mAb G19.4 (2 µg/ml) at time=1.5 min., followed by avidin (8 µg/ml) added at time=5.5 min. (—) This was compared with the same cross-linking of the CD3 receptor in the presence of anti-CD45 mAb 9.4 (10 µg/ml) (-•-) or to biotin-conjugated anti-CD45 mAb 9.4 (10 µg/ml) followed by avidin (48 µg) (•••••). An additional control of biotin-conjugated anti-CD45 mAb 9.4 (10 µg/ml) followed by avidin (40 µg/ml) was also used (----) (FIG. 10A);

2. The effect of 25 µg/ml of anti-CD3 mAb G19.4 (—) was compared to 50 g/ml of a CD3/CD45 heteroconjugate of anti-CD3 mAb G19-4 and anti-CD45 mAb 9.4 (•••••) (FIG. 10B);

3. The CD2 receptor was cross-linked with 10 µg/ml of biotin-conjugated anti-CD2 mAb 9.6 added at time=−3 min., followed by addition of 40 µg/ml of avidin at time=1.5 min. (—) (FIG. 10C);

4. The CD28 receptor was cross-linked with 10 µg/ml of biotin-conjugated anti-CD28 mAb 9.3 added at time=−3 min., followed by addition of 40 µg/ml of avidin at time=−3 min. (—) compared with simultaneous cross-linking of CD28 and CD45 receptors using 10 µg/ml of anti-CD28 mAb 9.3 and 10 µg/ml anti-CD45 mAb 9.4 added at time=−3 min. followed by addition of 80 µg/ml of avidin at time=1.5 min. (••••) (FIG. 10D); and 5. The CD4 receptor was cross-linked by addition of 10 µg/ml of biotin-conjugated anti-CD4 mAb G17-2 at time=−3 min., followed by 40 µg/ml of avidin added at time=1.5 min. (—). This was compared with simultaneous cross-linking of the CD4 and CD45 receptors by addition of 10 µg/ml of biotin-conjugated anti-CD4 mAb G17-2 and 10 µg/ml of biotin-conjugated anti-CD45 mAb 9.4 at time=−3 min., followed by addition of 80 µg/ml of avidin at time=1.5 min. (•••••). The comparison of biotin-conjugated anti-CD4 mAb G17-2 (10 µg/ml) plus anti-CD45 mAb 9.4 (10 µg/ml)

(not conjugated) followed by 40 μg/ml of avidin at time=1.5 min. is also shown (-•-) (FIG. 10E).

FIG. 10A–E presents the results of these experiments.

It was apparent that the increase in $[Ca^{2+}]_i$ seen after CD3, CD2 and CD28 crosslinking was inhibited by the presence of biotin conjugated 9.4. When 9.4 was not biotinylated, and thus not crosslinked by avidin, a small decrease in the extent of anti-CD3 induced calcium mobilization was still observed (FIG. 10A). Complete inhibition, however, appeared to require that CD45 and CD3 be brought into close proximity. Furthermore, a heteroconjugate of anti-CD45 and anti-CD3 was unable to directly increase $[Ca^{2+}]_i$ (FIG. 10B) even though immunofluoresence assays with an anti-mouse immunoglobulin demonstrated that the heteroconjugate could bind to both receptors on the cell surface (data not shown) and 25 μg of anti-CD3 could elicit a strong calcium response. CD45R mAbs such as 3AC5 were able to partially inhibit $[Ca^{2+}]_i$ responses when ligated to mAbs reactive with the cell receptors, such as illustrated for CD2 (FIG. 10C). The partial inhibition afforded by CD45R mAb may reflect the expression of CD45R isoform on some but not all T cells (Ledbetter, supra). In contrast to the inhibitory effects on CD3, CD2 and CD28, ligation of CD45 to CD4 gave a strong and reproducible augmentation of signalling as compared to when CD4 is crosslinked to itself (FIG. 10E). This occurred without an increase in the number of responding cells, showing that the same CD4 positive cells were more responsive following ligation of CD45 and CD4. Thus, CD45 appears to either up or down-regulate transmembrane signalling depending on the receptor with which it is interacting.

Previous studies of CD45 suggested that it may function to either up- or down-regulate lymphocyte activity (Ledbetter, suipra; Harp, supra and Martorell, supra). Soluble mAbs to CD45 or CD45R are co-stimulatory with PHA or anti-CD3 attached to beads in increasing IL-2 production, IL-2 receptor expression, and T-cell proliferation. Soluble anti-CD45 can act cooperatively with CD2 or CD28 mAb (Table VI). These co-stimulatory effects are restricted to CD4+ cells and are not seen with CD8+ cells which do not express CD4. This may be due in part to the fact that CD45 has a characteristic effect on CD4 distinct from its action on other cell surface antigens such as CD3 or CD2; when CD45 is brought into close association with CD4, it acts to accelerate and increase the calcium signal transmitted via CD4 while inhibiting signal transduction when coupled to CD3 and CD2 (FIG. 10).

The above example (4) demonstrates that the inhibitory effects of anti-CD45 are most clearly demonstrated under conditions that place CD45 into close contact with signal transducing elements such as the T cell receptors CD2, CD3, CD5 or CD28 as demonstrated by use of the CD4/CD45 heteroconjugate of the invention. The anti-CD45 antigen can act very early in lymphocyte activation, inhibiting the mobilization of intracellular free calcium normally detectable within 30 to 60 sec. The enhancing effects of anti-CD45 are also demonstrated by placing one CD45 receptor into proximity with the CD4 receptor. These results suggest that heteroconjugates containing molecules reactive with receptors on lymphocytes can provide an alternative method for inducing interaction between the receptors to enhance or inhibit activation and function of the lymphocytes, including T cells and B cells.

EXAMPLE 5

The following example describes the preparation of bispecific antibodies ("bsmAbs") of the invention. According to this embodiment, bispecific antibodies are prepared by fusing various hybridoma cell lines producing mAb reactive with CD antigens.

I. Preparation of Hybridomas a) Parent hybridoma cell lines reactive with human CD antigens were as follows:

| mAb   | mAb specificity | mAb isotype       |
|-------|-----------------|-------------------|
| 9.6   | CD2             | IgG2a[1]          |
| G19-4 | CD3             | IgG1[2]           |
| G19-2 | CD4             | IgG1[3]           |
| 10.2  | CD5             | IgG2a[1]          |
| G10-1 | CD8             | IgG2a[2]          |
| 9.3   | CD28            | IgG2a[2]          |
| 9.4   | CD45            | IaG2a[4]          |

[1]Cell line referenced in Example 2, supra.
[2]Cell line referenced in Example 1, supra.
[3]Cell line referenced in Linsley et al., Virology 62:3695–3702 (1988).
[4]Cell line referenced in Example 3, supra.

All hybridoma cell lines were mycoplasma-free at the time of fusion and were obtained from cell banks at Oncogen, Seattle, Wash.

The parent hybridoma cell lines have been deposited with the American Type Culture Collection (ATCC), 12301 Parklawn Drive, Rockville, Md. 20852 under the Budapest Treaty and have there been identified as follows:

| Hybridoma |            | ATCC Accession No. | Deposit Date        |
|-----------|------------|--------------------|---------------------|
| 9.6       | (anti-CD2) | HB 10267           | October 20, 1989    |
| G19-4     | (anti-CD3) | HB9536             | September 15, 1987  |
| G19-2     | (anti-CD4) | HB10324            | January 16, 1990    |
| 10.2      | (anti-CD5) | HB10269            | October 20, 1989    |
| G10-1     | (anti-CD8) | HB 10268           | October 20, 1989    |
| 9.3       | (anti-CD28)| HB 10271           | October 20, 1989    |
| 9.4       | (anti-CD45)| HB 10270           | October 20, 1989    | b) Selection of HAT-sensitive "master hybridoma" myeloma lines: The hybridomas G19-4 (anti-CD3), 10.2 (anti-CD5), 9.3 (anti-CD28) and 9.4 (anti-CD45) were chosen as "master" cell lines and were selected for HGPRT deficiency so that each could be fused to any of the other HGPRT+ hybridoma lines desired. Each cell line was cultured with increasing concentrations of the toxic guanine analogues 8-azaguanine or 6-thioguanine to a final concentration of 3 μg/ml. Cells which were HGPRT-deficient survived the treatment due to their inability to metabolize the toxic analogues. The cells were cloned once in semi-solid agar, as follows.

Cell lines were cloned by suspending individual cells in a matrix of semi-solid agar as described by Clark et al., Methods in Hematology 13:1–20, (1986). In summary, a nutrient layer was prepared by mixing equal parts of 2× concentrated Iscove's Modified Dulbecco's Medium (IMDM) and 1.1% agar (w/v) in water (boiled and cooled to 45° C.), with 1 part fetal calf serum (FCS) added to 9 parts of the IMDM/agar mixture. Two ml of the solution were pipetted into each of 35 mm Falcon tissue culture dishes (Becton Dickinson, Oxnard, Calif.) and allowed to set. Five serial fivefold dilutions of hybridoma cell suspension were made from an initial dilution of 0.2 ml cells in 1.0 ml IMDM supplemented with 10% FCS. One ml of the remaining IMDM/agar mixture was added to each dilution, mixed quickly, transferred to one of the nutrient layers, and allowed to set. The cells were cultured for 7–10 days and visible clones were removed from the agar and cultured in IMDM supplemented with 10% FCS.

c) Testing for mAb production:

Prior to fusion, sub-clones of the original hybrid myeloma cell lines were tested for mAb production, and only those producing a high titer of mAb were used for fusions. Supernatants collected from the sub-clones were incubated with normal peripheral blood lymphocytes (PBLs) and FITC-labelled goat anti-mouse Ig (TAGO, Burlingame, Calif.) was used in conjunction with a fluorescence-activated cell sorter (EPICS V) to quantitate the mAb binding. Supernatants were also assayed by inhibition of binding of FITC-labelled mAb isolated from the original hybridoma cultures.

d) Production of hybrid hybridomas by cell-cell fusion:

The fusion protocol used was adapted slightly from that described by Clark et al., "T-cell killing of target cells induced by hybrid antibodies: A comparison of two bi-specific monoclonal antibodies", *J. Natl. Cancer Inst.* 79:1393–1401, (1987); and Clark et al, "Hybrid antibodies for therapy", *Prop. Allergy* 45:31–49, (1988). In summary, $1.5 \times 10^7$ to $3 \times 10^7$ viable cells of the HAT-resistant fusion partner in exponential growth phase were washed twice with ice-cold IMDM (no serum added). The cells were resuspended in 10 ml ice-cold PBS and 550 µl of a 100 mM stock solution of ice-cold iodoacetamide (Sigma, St. Louis, Mo.) in phosphate buffered saline (PBS) was added. The cells were incubated on ice for 23 min with the iodoacetamide and were mixed periodically. The cells were pelleted for 5 min at 1000 rpm in a centrifuge cooled to 4° C. and the iodoacetamide/PBS was aspirated. The pre-selected HAT-sensitive cells, similarly in exponential growth and washed twice in serum-less IMDM, were pelleted at room temperature with the iodoacetamide-treated cells in a ratio of 3:1 or 4:1. The medium was aspirated, and the cells were placed in a 37° C. water bath for 10 seconds prior to the fusion. Cell fusion was induced by adding 1.0 ml of 50% PEG 1450 in PBS (warmed to 37° C.) for 1 min with stirring, allowing cells to rest 30 seconds, then adding 25 ml of serum-less IMDM warmed to 37° C. over the final 30 seconds. The cells were pelleted at 800 rpm, resuspended gently in IMDM supplemented with 10% FCS, plated in 24×2 ml culture plates (Costar, Cambridge, Mass.) at $5 \times 10^5$ to $7.5 \times 10^5$ cells/well, and cultured at 37° C. HAT selection was commenced 24 h later by feeding the cultures for 3 successive days with IMDM supplemented with 10% FCS and HAT. Fusions are shown in Table VIII:

TABLE VIII

| Fusions | |
|---|---|
| Parental hybridoma 1 (HAT-sensitive) | Parental hybridoma 2 |
| G19-4 (CD3) | 9.6 (CD2)[1] |
| G19-4 (CD3) | G19-2 (CD4) |
| G19-4 (CD3) | G10-1 (CD8) |
| G19-4 (CD3) | 9.4 (CD45) |
| 10.2 (CD5) | G19-2 (CD4) |
| 10.2 (CD5) | G10-1 (CD8) |
| 10.2 (CD5) | 9.4 (CD45) |
| 9.4 (CD45) | G19-2 (CD4) |
| 9.4 (CD45) | G10-1 (CD8) |
| 9.6 (CD2) | 9.3 (CD28) |

[1]The antigen to which the corresponding mAbs bind is indicated in parentheses.

II. Screening for Wells Containing Both Parental mAb Activities

Because hybrid hybridomas produce both forms of parental antibody in addition to various forms of hybrid antibody molecules, one of which is the bispecific form (e.g. see FIG. 11) it was possible to rapidly screen the fusion supernatants for wells which contained both parental mAb activities. As shown in FIG. 11, each of the two parental species, denoted $L_1H_1H_1L_1$ and $L_2H_2H_2L_2$ (where H and L denote the antibody heavy and light chains) are produced by the hybrid hybridoma, along with various hybrid mixtures. One is the functionally bispecific form $L_1H_1H_2L_2$ consisting of homologously paired heavy and light chains derived from each parent. Four forms are functionally monovalent for one or the other parental specificity: $L_1H_1H_2L_1$, $L_1H_1H_1$, $L_2$, $L_2H_1H_2L_2$, $L_1H_2H_2L_2$. The remaining forms are inactive due to inappropriate pairing of heavy and light chains on both halves of the antibody molecule ($L_1H_2H_1L_2$, $L_1H_2H_2L_1$, and $L_2H_1H_1L_2$). T cells were incubated with the fusion supernatants, then a mixture of the two parental mAbs (each of which had been pre-tagged with either a green ("FITC") or red (phycoerythrin, "PE") fluorescence marker) was added. The cells were washed free of unbound mAb, and fluorescence activated cell sorting ("FACS") using an EPICS V cell sorter was used to measure the amount of inhibition of binding of the green and/or red tagged parental mAbs. Inhibition of both green and red fluorescence indicated that both parental mAbs were present and functional in the supernatant isolated from the corresponding well. Since the iodoacetamide poisoning during the fusion procedure and subsequent growth in HAT medium select against both unfused parental hybridomas, detection of both parental mAbs in a single fusion well suggested the presence of hybrid antibody molecules in addition to the presence of parental antibody (ie. the molecules were being produced by a hybrid hybridoma). This procedure, performed as follows, quickly defined wells of interest which were cloned in semi-solid agar (Example 5, section I "b"). The wells were then characterized further for functional activity in regulating lymphocyte activation.

Human PBLs were incubated with supernatants from the fusion cultures, or with controls of either parental cell supernatant alone, or a mixture of the two, for 30 min. at 0° C. The supernatants were aspirated and a mixture of phycoerythrin (PE)-labelled first parental mAb and a FITC-labelled second parental mAb were added, and incubated with the cells for 30 min. at 0° C. Non-binding mAbs were then removed by washing and inhibition of binding of the tagged parental mAbs to the T cells was quantified using an EPICS V fluorescence activated cell sorter (FACS). While controls of supernatant from either parental mAb blocked the binding of the corresponding tagged mAb only, in comparison to the staining observed without blocking mAb, only wells containing hybrid hybridomas were able to block the binding of both tagged parental mAbs.

III. Screening for wells containing bsmAbs

The fusions between two parental hybridomas producing mAbs of different isotype facilitated the characterization of the fusion supernatants by ELISA. The presence of bsmAbs was supported by detection of mixed immunoglobulin heavy chain antibodies.

For example, when testing fusions such as CD3/CD8 which contained mixed IgGl/IgG2a heavy chains, the following procedure was used.

Falcon flat-bottom 96 well flexible microtiter plates were coated with goat anti-mouse IgGl-specific antiserum (Fisher, Orangeburg, N.Y.) at 1 µg/ml in PBS for 24 h at 4° C. The plates were blocked with PBS/1% BSA/0.1% rabbit serum/0.1% azide at 4° C. until use. Culture supernatants (50 µl) from IgGl/IgG2a fusions or 25+25 µl of a 1:1 mixture or 50 µl of the corresponding heteroconjugate at 5 µg/ml were incubated in the goat-anti-mouse IgGl-coated wells for 30 min at room temperature, then washed with PBS/0.1% BSA. Mixed heavy chain combinations were detected with 50 μl biotinylated species specific goat anti-mouse IgG2a (Amersham, Amersham, U.K.) and 50 μl streptavidin-conjugated horseradish peroxidase (Amersham, Amersham, UK), followed by 100 μl of ortho-phenylenediamine (OPD) substrate (Zymed, San Francisco, Calif.) in 0.1 M citrate buffer, pH 5.5. The color reaction was stopped with 50 μl of 1.5 M $H_2SO_4$ and was quantified at $OD_{492}$ with a multiwell plate reader.

Table IX shows the results of a representative experiment. Figures given are duplicate values representing the increased color reaction of the OPD substrate in a positive result by ELISA.

TABLE IX

Detection of mixed heavy chain isotypes by ELISA

| Supernatant | Isotype | Anti-IgGl-coated microtiter plate + biotinylated anti-IgG2a ($OD_{492}$) |
|---|---|---|
| Medium only | — | 0;0[1] |
| G10-1 (CD8) | IgG2a | 0;0 |
| G19-4 (CD3) | IgG1 | 1;1 |
| G19-4 + G10-1 (CD3 + CD8 mix) | IgG1 and IgG2a | 2;2 |
| G19-4 + G10-1 (CD3/CD8 HC) | IgG1/IgG2a | 60;52 |
| HFD 112.1 (CD3/CD8 Hybrid) | IgG1/IgG2a | 50;52 |

[1]Values are for duplicate experiments.

Only the chemically conjugated IgGl/IgG2a heavy chains of the G19-4/G10-1 (CD3/CD8) heteroconjugate, or the naturally associated IgGl/IgG2a heavy chains of the HFD112.1 CD3/CD8 hybrid bispecific antibody were detected in this assay. In comparison, controls of either parent mAb alone, or an artificial mixture of the two parental mAbs, were not detected because (a) the G19-4 (IgGl) bound to the microtiter plate but could not be detected by biotinylated anti-IgG2a and streptavidin-conjugated horseradish peroxidase, and (b) G10-1(IgG2a) did not bind to the anti-IgGl-coated microtitre plate.

As disclosed above, the hybrid hybridomas of the invention producing bispecific antibodies from the above-described fusions have been deposited with the ATCC.

EXAMPLE 6

This example describes the characterization of the bsmAbs prepared as described in Example 5.

I. Induction of Calcium Mobilization:

Human PBLs were loaded with the calcium-binding dye indo-1 (Molecular Probes, Eugene, Oreg.). Mobilization of calcium was monitored by flow cytometry using an Ortho model 50 HH/2150 cell sorter (Ortho Diagnostics, Westwood, Mass.) as described previously [Rabinovitch et al., "Heterogeneity among T cells in intracellular free calcium responses after mitogen stimulation with PHA or anti-CD3. Simultaneous use of indo-1 and immunofluorescence with flow cytometry", *J. Immunol.*, 137:952–961 (1986)] and in Example 1. For each assay, $1 \times 10^6$ PBLs were pre-incubated at 37° C. for 10 min in RPMI 1640 medium supplemented with 10% FCS prior to the analysis, and a selected volume of culture supernatant from the hybrid hybridoma fusion wells were added after establishing a baseline of 1 min duration.

Figure 12:
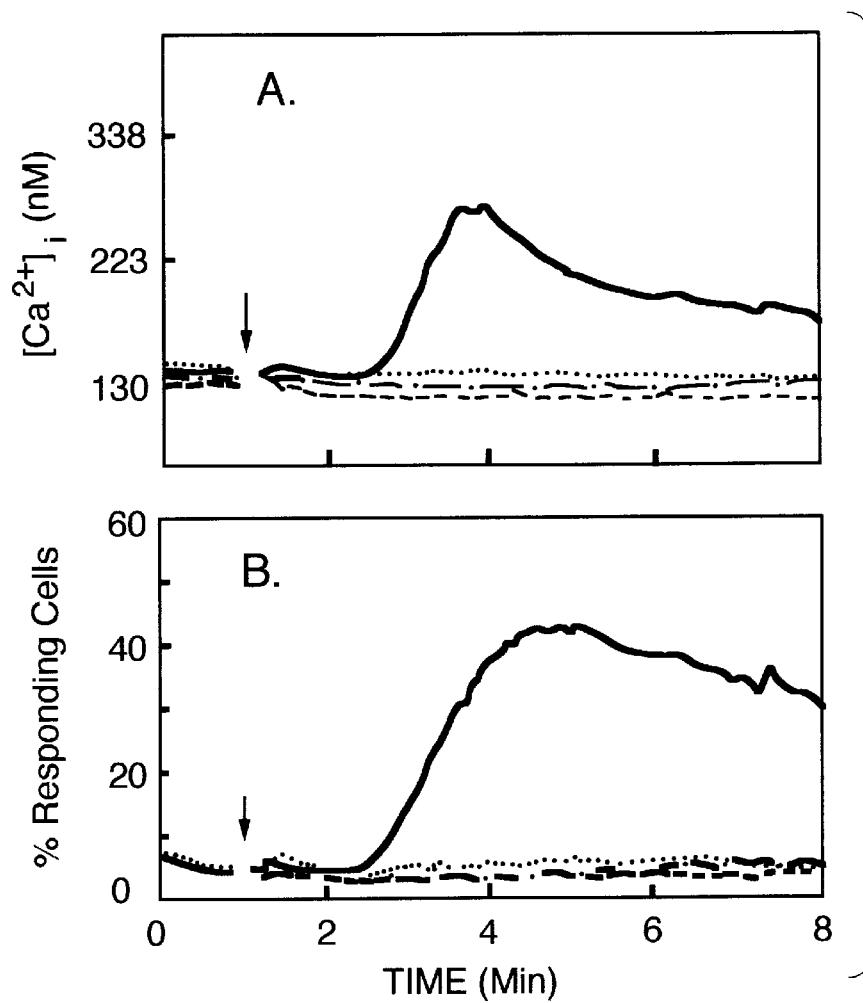
FIG. 12 (A–B) are graphs depicting the regulation of signal transduction in T cells by the bispecific antibodies of the invention as determined by increases in $[Ca^{2+}]_i$ as described in Example 6, infra. (12A=mean $[Ca^{2+}]_i$; 12B= percentage of responding cells. Arrows indicate time of addition of antibodies (—)=45 µg of CD4/CD5 bispecific antibody; (•••••)=45 µg CD5 antibody alone; (----)=45 µg CD4 antibody alone; (-•-•-•)=a mixture of 22.5µ CD5 antibody plus 22.5 µg CD4 antibody).

The response of T cells to the CD5/CD4 bispecific antibody and to the corresponding controls is illustrated in FIG. 12. PBL were enriched for T cells by removal of the majority of the monocytes by incubation on plastic surfaces and removal of the B cells by passage over nylon wool columns, as described earlier (Example 4). When T cells were incubated with 45 μg of CD5/CD4 bispecific antibody (prepared from a 50% ammonium sulphate precipitation of spent culture supernatant from the corresponding hybrid hybridoma), induction of calcium mobilization was observed. The $[Ca^{2+}]_i$ increased and peaked approximately 3 min after addition of the CD5/CD4 antibody (panel A) with over 40% of the cells responding (panel B). In contrast, neither the CD4 parental mAb (45μg) nor the CD5 parental mAb (45μg) elicited calcium mobilization. The control of artificially mixed (but unconjugated) parental CD4 and CD5 mAbs (22.5 μg of each) also did not induce a calcium response. Similar results were observed with the CD3/CD8 and with the CD5/CD8 bispecific antibodies in comparison to the appropriate controls.

II. Induction of cellular proliferation in the presence of bispecific CD3/CD2. CD3/CD4 and CD3/CD8 antibodies One of the ultimate goals for in vivo therapy is the ability to harness lymphocyte activation such that activation and proliferation of the whole lymphocyte population, or specific lymphocyte subsets can be achieved. This goal may become attainable with the bispecific antibodies of the invention, as indicated by the following in vitro proliferation studies.

PBLs used in these assays were enriched for T cells by depletion of the majority of monocytes by their adherence to plastic surfaces followed by passage of the non-adherent cells over nylon wool columns to deplete B cells as described earlier (Example 4). The non-adherent cells were plated into flat-bottom 96-well microtiter tissue culture plates in RPMI 1640 medium supplemented with 15% human AB serum (Pel-Freez, Brown Deer, Wis.) at a concentration of $1 \times 10^5$ cells per well. Cultures were set up in triplicate in a total volume of 200 μl/well. Culture supernatants from hybrid hybridomas and from parental controls were used at 50 μl/well and heteroconjugated mAb controls were used at a final concentration of 2 μg/ml. Anti-CD28 mAb 9.3 was used at a final concentration of 1 μg/ml in wells as indicated. The cells were cultured for 72 hr and proliferation was measured by uptake of [$^3$H]thymidine (6.7 Ci/mmol, New England Nuclear, Boston, Mass.). After a 6 hr pulse with 1.0 μCi [$^3$H]thymidine per well, cells were harvested onto glass filters and radioactivity was determined by scintillation counting.

Table X summarizes the results, which are representative of replicate experiments using PBL from different donors. Results are shown as counts per minute (cpm) of triplicate cultures +the standard error of the mean (S.E.M).

TABLE X

Induction of cellular proliferation by bispecific CD3/CD4, CD3/CD8, and CD3/CD2 mAbs in the presence of soluble anti-CD28.

| | [$^3$H]Thymidine uptake (cpm × $10^{-3}$)[1] | |
|---|---|---|
| Supernatant/Control | + Medium | + 9.3 (CD28) 1 μg/ml |
| G19-4 (CD3) | 0.1 | 0.2 |
| G19-2 (CD4) | 0.0 | 0.0 |
| G19-4 + G19-2(CD3 + CD4) | 0.1 | 2.7 |
| G19-4/G19-2 (CD3/CD4 HC) | 0.6 | 190.8 |
| HFA 19.2 (CD3/CD4 HYB) | 1.0 | 240.6 |
| G19-4 (CD3) | 0.1 | 0.2 |
| G10-1 (CD8) | 0.1 | 0.0 |

TABLE X-continued

Induction of cellular proliferation by bispecific CD3/CD4, CD3/CD8, and CD3/CD2 mAbs in the presence of soluble anti-CD28.

| | [$^3$H]Thymidine uptake (cpm × $10^{-3}$)[1] | |
|---|---|---|
| Supernatant/Control | + Medium | + 9.3 (CD28) 1 µg/ml |
| G19-4 + G10-1 (CD3 + CD8) | 0.1 | 0.6 |
| G19-4/G10-1 (CD3/CD8 HC) | 0.2 | 10.8 |
| HFD 112.1 (CD3/CD8 HYB) | 0.1 | 17.8 |
| G19-4 (CD3) | 0.1 | 0.2 |
| 9.6 (CD2) | 0.1 | 0.0 |
| G19-4 + 9.6 (CD3 + CD2) | 0.1 | 0.2 |
| G19-4/9.6 (CD3/CD2 HC) | N.D. | N.D. |
| HFE 16.4 (CD3/CD2 HYB) | 1.6 | 155.5 |
| Medium (Background) | 0.1 | 0.1 |

[1]S.E.M. was <10%.

The data summarized in Table X demonstrate that even though none of the bispecific mAbs tested could induce proliferation on their own (with the possible exception of the HFE 16.4 (CD3/CD2) hybrid which induces very low but consistent levels of proliferation without requiring the addition of other factors), the anti-CD28 mAb 9.3 synergized with the hybrid antibodies HFA 19.2 (CD3/CD4 HYB), HFD112.1 (CD3/CD8 HYB) and HFE 16.4 (CD3/CD4 HYB), HFD112.1 (CD3/CD2 HYB). Presumably the CD3/CD4 hybrid is preferentially stimulating the CD4+T cell subset and the CD3/CD8 hybrid is preferentially stimulating the CD8+ T cells, while the CD3/CD2 hybrid is capable of stimulating proliferation of both T cell subsets since CD2 is a pan-T cell marker. In contrast, neither parental mAb used alone, nor an artificial mixture of both parental mAbs mixed together, was able to induce cellular proliferation.

III. Induction of protein tyrosine kinase (PTK) activity:

Activation of PTK in T cells is an early activation event which has been observed following perturbation of the T cell receptor complex. [Samelson et al., "T cell antigen receptor phosphorylation induced by an anti-receptor antibody", *J. Immunol.* 139:2708, (1987); Hsi, et al., "T cell activation induces rapid tyrosine phosphorylation of a limited number of cellular substrates", *J. Biol. Chem.*, 264:10836 (1989)]. Activation of PTK was investigated using the CEM T cell line obtained from the Oncogen (Seattle, Wash.) cell bank. 5×10$^6$ CD3$^+$ CEM T cells were stimulated with 1.0 ml of culture supernatant from the CD3/CD4, CD3/CD8, CD5/CD4 or CD5/CD8 hybrid hybridomas, or from the corresponding parental hybridomas, or with 10 µg/ml of the corresponding heteroconjugates over a time-course of 0, 2, and 5 min at 37° C. Whole cell lysates were prepared by pelleting the cells for 3 sec in a microfuge, aspirating the stimulus, and resuspending the pellet in 300 µl of boiling SDS sample buffer. The DNA was sheared and equivalent amounts of protein were loaded onto 10% polyacrylamide gels and electrophoresed overnight. Protein from the gels was transferred to Immobilon (Millipore Corp., Bedford, Mass.) for 2 h at 4° C. Immunoblots were incubated with 0.25/µg/ml of anti-phosphotyrosine antibody [Kamps et al., "Identification of multiple novel polypeptide substrates of the V-src, V-yes, V-fps, V-ros, and V-erb-B oncogenic tyrosine protein kinases utilizing antisera against phospho-tyrosine" *Oncogene* 2:305 (1988)] followed by washing and development with 1 µCi/ml high specific activity $^{125}$I-protein A (ICN Biomedicals, Costa Mesa, Calif.). Prestained high molecular weight markers (Bethesda Research Laboratory, Bethesda, Md.) were included on each gel.

The protein tyrosine kinase activity of resting CEM T cells in response to stimuli including CD3, CD4 or CD8 mAb alone, and to reagents which crosslink pairs of the antigens together, i.e. heteroconjugated mAbs (HC) or bispecific hybrid mAbs (HYB), is shown in FIG. 13. In FIG. 13A, the substrates which are consitutively phosphorylated on tyrosine are illustrated. In the presence of supernatant containing CD3 mAb only (FIG. 13B), a low level of phosphorylation of a 37kDa protein is detected and several substrates show increased phosphorylation in comparison tc FIG. 13A. Incubation of the cells with CD4 mAb alone (FIG. 13C) or with CD8 mAb alone (FIG. 13D) does not induce tyrosine kinase activity. Exposure of the cells to a mixture of CD3 and CD4 antibodies (FIG. 13E) or a mixture of CD3 and CD8 antibodies (FIG. 13H) induces phosphorylation of the same protein as did CD3 mAb alone, but to a stronger degree. The CD3/CD4 hybrid (bispecific) antibody (FIG. 13F) and the CD3/CD8 bispecific hybrid antibody (FIG. 13I) both induced rapid and strong phosphorylation of the 37 kDa protein.

The CD5/CD4 and CD5/CD8 bispecific hybrid antibodies were also able to activate protein tyrosine kinase activity (FIGS. 14 and 15, respectively). Both of these bispecific hybrid antibodies induced phosphorylations of substrates of 117 kDa, 99 kDa, 73 kDa, 59 kDa and 52 kDa, in comparison to controls of either parental mAb alone, or to a mixture of the parental mAbs. Interestingly, the CD5/CD4 bispecific mAb induced phosphorylation of a protein at 62 kDa (FIG. 14D). These results suggest that hybrid bispecific antibodies are able to induce molecular interactions on the T cell surface which appear to regulate tyrosine kinase activity, which in turn may play an important role in T cell activation [Rudd et al., *Proc. Natl. Acad. Sci. USA* 85:5190–5194 (1988); Barber et al., *Proc. Natl. Acad. Sci. USA* 86:3277–3281 (1989); Samelson et al., *J. Immunol.* 139:2708–2713 (1987)].

The hybrid hybridomas produced as described herein express both sets of parental immunoglobulin heavy and light chain genes. The encoded proteins are free to associate into mixed species of antibody molecules. One of the hybrid forms is the bispecific monoclonal antibody (bsmAb) of the invention. BsmAbs are molecules which are functionally monovalent for each of the parental mAb specificities. A unique property of the bsmAbs in comparison to the other mixed antibody molecules is their ability to bind to two antigens simultaneously. Where the two antigens that bind to the bsmAbs are surface CD receptors involved in T cell responses, the bsmAbs of the invention have been shown to enhance and inhibit T cell responses in vitro.

In comparison to heteroconjugates, bispecific mAbs may be desirable for in vivo therapy, because they are smaller in size and because they may not possess a functional Fc-binding portion [e.g. see Clark et al.,*JNCI* 79:1393–1401 (1987)]. The large size of heteroconjugates makes them targets for clearance by cells of the reticuloendothelial system (RES). Bispecific antibodies may also be preferred because of the inherent disadvantages associated with heteroconjugates including batch variation and reduced binding activity due to the conjugation procedure. Conjugating F(ab')2 or even Fab together would reduce the size of the heteroconjugate molecule and would remove the Fc-binding portions, but preparation of antibody fragments is time-consuming and the yield is often low.

The results presented herein demonstrate that bsmAbs supernatants from the hybrid hybridomas possess the functional activity predicted previously by the corresponding heteroconjugates, also described herein, even though the bsmAbs were not purified from the competing forms of mixed and parental mAbs. For example, both heteroconjugates and fusion supernatants of CD3/CD8, CD5/CD4, and CD5/CD8 induced increases in $[Ca^{2+}]_i$. The CD3/CD8, the CD3/CD4, and the CD3/CD2 combinations induced proliferation in the presence of anti-CD28 mAb 9.3, as did the corresponding heteroconjugates. Combinations of CD5/CD4 and CD5/CD8 did not induce proliferation, but did mobilize $[Ca^{2+}]_i$ effectively. This result is entirely consistent with data obtained from crosslinking CD5 and CD4 or CD5 and CD8 antigens together with heteroconjugated mAbs. Calcium mobilization in the presence of CD3/CD2 heteroconjugates was more dependent on the degree of aggregation than the response elicited in the presence of CD3/CD4 and CD3/CD8. Supernatants from CD3/CD2 fusions did not induce calcium mobilization in the time frame analyzed (up to 10 min), but were mitogenic in cultures supplemented with 9.3. The activities of the hybrid hybridoma supernatants were distinguishable from controls of either parental hybridoma supernatant alone, or an artificial (unfused) mixture of the two parental mAbs. These data suggest that the bispecific hybrid antibodies can induce molecular interactions on the cell surface which are similar to those induced by the heteroconjugates. However, as suggested in this invention, the smaller bispecific molecules would be advantageous for therapeutic applications. These interactions can regulate the activation of lymphocytes in vitro, which suggests that similar interactions may be useful for in vivo regulation of lymphocyte activation.

Because the bsmabs were used as unpurified hybrid hybridoma supernatants, the activity of the bsmAbs is expected to increase significantly following purification. Although purification protocols may vary for each bsmAb depending on characteristics of the immunoglobulin heavy and light chains, such as charge and isotype, periodic sub-cloning of the hybrid hybridoma will ensure that expression of all four immunoglobulin chains remains stable.

In general, mixed heavy chain isotypes are desirable since isotype-specific reagents are commercially available for purification (e.g. conjugated to a sepharose column). The bsmAbs may be purified by sequential elution from a column that binds the first parental mAb (plus the bsmab and few contaminating species), followed by elution from a column that binds the second parental mAb. Because the parental mAb 2 does not bind to the first column, and parental mAb 1 does not bind to the second column, the eluted species will be enriched for bsmabs.

While we have hereinbefore presented a number of embodiments of the invention, it is apparent that the basic construction of this invention can be altered to provide still other embodiments, e.g., other heteroconjugate or bispecific antibody combinations which lead to the enhanced activation of lymphocytes, or to the inhibition of the function of lymphocytes. Therefore, it will be appreciated that the scope of this invention is to be defined by the claims appended hereto rather than by the specific embodiments which have been presented hereinbefore by way of example.

We claim:

1. A heteroconjugate useful in the regulation of lymphocytes comprising two molecules that specifically bind to different antigens located on the surface of a single lymphocyte, the different antigens binding to antigen-binding sites within the heteroconjugate that recognize epitopes of different structure, said antigens affecting calcium mobilization when brought into proximity of each other, and said molecules cross-linked to each other, said heteroconjugate regulating lymphocyte activity when the molecules, in soluble form, are bound to the surface of a single lymphocyte, with the proviso that said heteroconjugate is not a CD3/CD4 heteroconjugate or a CD3/CD8 heteroconjugate.

2. The heteroconjugate of claim 1, wherein the antigens are CD antigens on the surface of a T lymphocyte.

3. The heteroconjugate of claim 1, wherein the antigens are CD antigens on the surface of a B lymphocyte.

4. The heteroconjugate of claim 1, wherein one of the molecules of the heteroconjugate specifically binds to the T cell receptor or its associated CD3 antigen.

5. The heteroconjugate of claim 1, wherein one of the molecules of the heteroconjugate specifically binds to the CD5 T cell surface antigen.

6. The heteroconjugate of claim 1, wherein said molecules are antibodies.

7. The heteroconjugate of claim 6 where the antibodies are composed of antibody fragments selected from the group consisting of Fab and F(ab')$_2$ fragments, the two antibody fragments being positioned in the heteroconjugate so that the two CD antigens targeted by the heteroconjugate are both located on one lymphocyte.

8. The antibody heteroconjugate of claim 6, wherein the antibodies are monoclonal, the two antibodies being positioned in the heteroconjugate so that the two CD antigens targeted by the heteroconjugate are both located on one lymphocyte.

9. The heteroconjugate of claim 1, wherein one of the molecules of the heteroconjugate binds specifically to CD45 antigen or isoforms of the CD45 antigen, the two molecules of the heteroconjugate being positioned in the heteroconjugate so that the two CD two antigens targeted by the heteroconjugate are both located on one lymphocyte.

10. The heteroconjugate of claim 1, wherein said molecules are ligands specifically binding to lymphocyte surface antigens, the two ligands of the heteroconjugate being positioned in the heteroconjugate so that the two CD antigens targeted by the heteroconjugate are both located on one lymphocyte.

11. The heteroconjugate of claim 1 wherein said lymphocytes are T lymphocytes and said heteroconjugate activates said T lymphocytes.

12. An antibody heteroconjugate selected from the group consisting of CD3/CD2, CD3/CD6 and CD3/CD7, the two antibodies of the heteroconjugate being positioned in the heteroconjugate so that the two different CD antigens binding to antigen-binding sites within the heteroconjugate that recognize epitopes of different structure and targeted by the heteroconjugate are both located on one lymphocyte when the heteroconjugate is in soluble form.

13. An antibody heteroconjugate selected from the group consisting of CD5/CD4, CD5/CD6 and CD5/CD8, the two antibodies of the heteroconjugate being positioned in the heteroconjugate so that the two different CD antigens binding to antigen-binding sites within the heteroconjugate that recognize epitopes of different structure and targeted by the heteroconjugate are both located on one lymphocyte when the heteroconjugate is in soluble form.

14. An antibody heteroconjugate CD3/CD45, the two antibodies of the heteroconjugate being positioned in the heteroconjugate so that two different CD antigens binding to antigen-binding sites within the heteroconjugate that recognize epitopes of different structure and targeted by the heteroconjugate are both located on one lymphocyte when the heteroconjugate is in soluble form.

15. The antibody heteroconjugate G19-4/9.4, the two antibodies of the heteroconjugate being positioned in the heteroconjugate so that the two different CD antigens binding to antigen-binding sites within the heteroconjugate that recognize epitopes of different structure and targeted by the heteroconjugate are both located on one lymphocyte when the heteroconjugate is in soluble form.

16. An antibody heteroconjugate selected from the group consisting of CD2/CD45, CD3/CD45, CD4/CD45, CD5/CD45, CD8/CD45, and CD28/CD45, the two antibodies of the heteroconjugate being positioned in the heteroconjugate so that the two CD antigens binding to antigen-binding sites within the heteroconjugate that recognize epitopes of different structure and targeted by the heteroconjugate are both located on one when the heteroconjugate is in soluble form.

17. An antibody heteroconjugate selected from the group consisting of CD2/CD45R, CD3/CD45R, CD4/CD45R, CD8/CD45R, CD5/CD45R, and CD28/CD45R, the two antibodies being positioned in the heteroconjugate so that the two different CD antigens binding to antigen-binding sites within the heteroconjugate that recognize epitopes of different structure and targeted by the heteroconjugate are both located on one lymphocyte when the heteroconjugate is in soluble form.

18. A heteroconjugate useful in the regulation of lymphocytes comprising two antibodies that specifically bind to different antigens located on the surface of a single lymphocyte, the different antigens binding to antigen-binding sites within the heteroconjugate that recognize epitopes of different structure, said antigens affecting calcium mobilization when brought into proximity to each other, and said molecules crosslinked to each other, said heteroconjugate regulating lymphocyte activity when the molecules, in soluble form, are bound to the surface of a single lymphocyte, with the proviso that said heteroconjugate is not a CD3/CD4 heteroconjugate or a CD3/CD8 heteroconjugate, wherein the antibodies are chimeric.

19. A bispecific antibody comprising a first binding region specifically binding to a first lymphocyte antigen and a second binding region specifically binding to a second lymphocyte antigen, the first and second lymphocyte antigens binding to binding regions within the bispecific antibody that recognize epitopes of different structure, said first and second lymphocyte antigens located on the surface of a single lymphocyte and said lymphocyte antigens affecting calcium mobilization when brought into proximity of each other, said bispecific antibody regulating lymphocyte activity when the first binding region and the second binding region are both bound to the first and second lymphocyte antigens on the surface of a single lymphocyte when the bispecific antibody is in soluble form, with the proviso that said bispecific antibody is not a CD3/CD4 bispecific antibody or a CD3/CD8 bispecific antibody.

20. The bispecific antibody of claim 19 wherein at least one of the first lymphocyte antigen and the second lymphocyte antigen is a CD antigen.

21. The bispecific antibody of claim 19, wherein one of the regions specifically binds to the CD3 antigen.

22. A bispecific antibody comprising a first binding region specifically binding to a first lymphocyte antigen and a second binding region specifically binding to a second lymphocyte antigen the first and second lymphocyte antigens binding to binding regions within the bispecific antibody that recognize epitopes of different structure, said first and second lymphocyte antigens located on the surface of a single lymphocyte and said lymphocyte antigens affecting calcium mobilization when brought into proximity of each other, said bispecific antibody regulating lymphocyte activity when the first binding region and the second binding region are both bound to the first and second lymphocyte antigens on the surface of a single lymphocyte when the bispecific antibody is in soluble form, wherein one of the regions specifically binds to the CD45 antigen or isoforms of the CD45 antigen.

23. A bispecific antibody selected from the group consisting of CD2/CD28, CD3/CD2, CD3/CD6, CD3/CD7, CD5/CD4, CD5/CD6 and CD5/CD8, the two different antigens binding to antigen-binding sites within the bispecific antibody that recognize epitopes of different structure, the two antigen-binding sites of the bispecific antibody being positioned in the bispecific antibody so that the two CD antigens targeted by the bispecific antibody are located on one lymphocyte when the bispecific antibody is in soluble form.

24. A bispecific antibody selected from the group consisting of CD2/CD45, CD3/CD45, CD4/CD45, CD5/CD45, CD8/CD45 and CD28/CD45, the two different CD antigens binding to antigen-binding sites within the bispecific antibody that recognize epitopes of different structure, the two antigen-binding sites of the bispecific antibody being positioned on the bispecific antibody so that the two CD antigens targeted by the bispecific antibody are located on one lymphocyte when the bispecific antibody is in soluble form.

25. A bispecific antibody selected from the group consisting of CD2/CD45R, CD3/CD45R, CD4/CD45R, CD5/CD45R, CD8/CD45R and CD28/CD45R, two different CD antigens binding to antigen-binding sites within the bispecific antibody that recognize epitopes of different structure, the two antigen-binding sites of the bispecific antibody being positioned in the bispecific antibody so that the two CD antigens targeted by the bispecific antibody are located on one lymphocyte when the bispecific antibody is in soluble form.

26. A hybridoma producing a bispecific antibody comprising a first region specifically binding to a first lymphocyte antigen and a second region specifically binding to a different second lymphocyte antigen located on the surface of a single lymphocyte, the first and second antigens affecting calcium mobilization when brought into proximity of each other, said bispecific antibody regulating lymphocyte activity when the first binding region and the second binding region are both bound to the surface of a single lymphocyte when the bispecific antibody is in soluble form, the two different antigens binding to antigen-binding sites within the bispecific antibody produced by the hybridoma that recognize epitopes of different structure, with the proviso that the bispecific antibody produced by the hybridoma is not a CD3/CD4 bispecific antibody or a CD3/CD8 bispecific antibody.

27. A hybridoma producing a bispecific antibody comprising a first region specifically binding to a first lymphocyte antigen and a second region specifically binding to a different second lymphocyte antigen located on the surface of a single lymphocyte, the first and second antigens affecting calcium mobilization when brought into proximity of each other, said bispecific antibody regulating lymphocyte activity when the first binding region and the second binding region are both bound to the surface of a single lymphocyte, the two different antigens binding to antigen-binding sites within the bispecific antibody produced by the hybridoma that recognize epitopes of different structure, wherein the hybridoma is HFC 80.6 (CD5/CD8).

28. A heteroconjugate useful in the regulation of lymphocytes comprising two molecules that specifically directly bind to different antigens on the surface of a single lymphocyte, said antigens affecting calcium mobilization when brought into proximity of each other, and said molecules cross-linked to each other by a heterobifunctional cross-linking agent selected from the group consisting of maleimidobutyryloxy succinimide and N-succinimidyl 3-(2-pyridyldithiol) propionate, said heteroconjugate regulating lymphocyte activity when the two molecules are bound to the surface of a single lymphocyte when the heteroconjugate is in soluble form, the two different antigens binding to antigen-binding sites that recognize epitopes of different structure on the heteroconjugate formed by the cross-linking of the two molecules, with the proviso that the heteroconjugate is not a CD3/CD8 heteroconjugate or a CD4/CD8 heteroconjugate.

* * * * *